United States Patent [19]

White et al.

[11] Patent Number: 5,605,799
[45] Date of Patent: Feb. 25, 1997

[54] SOMATIC MUTATIONS IN NEUROFIBROMATOSIS TYPE 1 GENE IN HUMAN TUMORS

[75] Inventors: Raymond L. White; Richard M. Cawthon; Ying Li, all of Salt Lake City, Utah

[73] Assignee: University of Utah Research Foundation, Salt Lake City, Utah

[21] Appl. No.: 411,389

[22] Filed: Mar. 28, 1995

Related U.S. Application Data

[63] Continuation of Ser. No. 47,088, Apr. 16, 1993, abandoned, which is a continuation-in-part of Ser. No. 551,531, Jul. 12, 1990, Pat. No. 5,227,292.

[51] Int. Cl.$^6$ .............................. C12Q 1/68; C12P 19/34; C07H 21/04; C12N 15/00

[52] U.S. Cl. .......................... 435/6; 435/91.1; 435/91.2; 435/91.51; 536/23.1; 536/23.5; 536/24.3; 536/24.31; 536/24.33; 536/25.3; 935/77; 935/78

[58] Field of Search ............................. 435/6, 91.1, 69.1, 435/320.1, 240, 183, 91.2, 91.5, 91.51; 536/18.7, 23.1, 23.4, 24.33, 25.3, 23.5, 24.3, 24.31; 935/77, 78; 436/94

[56] References Cited

U.S. PATENT DOCUMENTS 5,227,292   7/1993   White et al. ............................ 435/69.1

OTHER PUBLICATIONS

Webster's New World Dictionary of American English, Third College Edition, Neufeldt and Guralnik eds., Simon & Schuster, Inc., New York, New York, pp. 1075 and 1424. 1988.
O'Connell et al. Genomics. (7):547 (1990).
Fountain et al. Am J. Hum. Genet. 44:58—(1989).
Ledbetter et al. Am J. Hum. Genet. 44:20 (1989).
Menon et al. Genomics. (5):245 1989.
Fountain et al. Science 244:1085 (1989).
O'Connell et al. Science 244:1087 (1989).
Cawthon et al. Cell 62:193 (1990).
Pardue "In situ Hybridization" in Nucleic acid Hybridization, chapt 8 pp. 179–202, IRL press, Washington D.C. (1985).
Myers et al. Science 230:1242 (1985).
Cotton Biochem J. 263:1–10 1989.
Xu, G. et al. (1990). The Neurofibromatosis Type 1 Gene Encodes a Protein Related to GAP. Cell 62:599–608.

Buchberg, A. M. et al. (1990). Sequence Homology Shared by Neurofibromatosis Type–1 Gene and IRA–1 and IRA–2 Negative Regulators of the RAS Cyclic AMP Pathway. Nature 347:291–294.
Xu, G. et al. (1990). The Catalytic Domain of the Neurofibromatosis Type 1 Gene Product Stimulates ras GTPase and Complements ira Mutants of S. cerevisiae. Cell 63:835–841.
Martin, G. A. et al. (1990). The GAP–Related Domain of the Neurofibromatosis Type 1 Gene Product Interacts with ras p21. Cell 63:843–849.
Ballester, R. et al. (1990). The NF1 Locus Encodes a Protein Functionally Related to Mammalian GAP and Yeast IRA Proteins. Cell 63:851–859.
Moley, G. A. et al. (1991). Low Frequency of ras Gene Mutations in Neuroblastomas, Pheochromocytomas, and Medullary Tyroid Cancers. Cancer Res. 51:1596–1599.
Gibbs, J. B. (1991). Ras C–Terminal Processing Enzymes—New Drug Target? Cell 65:1–4.
Bollag, G. and McCormick, F. (1991). Differential Regulation of rasGAP and Neurofibromatosis Gene Product Activities. Nature 351:576–579.
Marchuk, D. A. et al. (1991). cDNA Cloning of the Type 1 Neurofibromatosis Gene: Complete Sequence of the NF1 Gene Product. Genomics 11:931–940.
Zhang, K. et al. (1991). Heterogeneous Amino Acids in Ras and Rap1A Specifying Sensitivity to GAP Proteins. Science 254:1630–1634.
DeClue, J. E. et al. (1990). Abnormal Regulation of Mammalian p21ras Contributes to Malignant Tumor Growth in von Recklinghausen (Type 1) Neurofibromatosis. Cell 69:265–273.
Bollag, G. and McCormick, F. (1992). NF is Enough of GAP. Nature 356:663–664.
Basu, T. N. et al. (1992). Aberrant Regulation of ras Proteins in Malignant Tumour Cells From Type 1 Neurofibromatosis Patients. Nature 356:713–715.
Li, Y. et al. (1992). Somatic Mutations in the Neurofibromatosis 1 Gene in Human Tumors. Cell 69:275–287.

Primary Examiner—Bradley L. Sisson
Attorney, Agent, or Firm—Venable, Baetjer, Howard & Civiletti, LLP

[57] ABSTRACT

The present invention is directed to somatic mutations of the NF1 gene which are found in human tumors. In addition, the present invention is directed to methods of screening humans to determine those having somatic mutations in the NF1 gene in tumors. Finally, the invention is directed to a method of treating a human having a tumor with a somatic mutation in the NF1 gene by restoring natural regulation of ras proteins.

14 Claims, 3 Drawing Sheets

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 10706 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: CDS
        ( B ) LOCATION: 287..8740

( i x ) FEATURE:
        ( A ) NAME/KEY: misc_feature
        ( B ) LOCATION: 3809..4888
        ( D ) OTHER INFORMATION: /function= "NF1 GRD"

( i x ) FEATURE:
        ( A ) NAME/KEY: misc_feature
        ( B ) LOCATION: 4451..4459
        ( D ) OTHER INFORMATION: /function= "Conserved area in GRD"

( x i ) SEQUENCE DESCRIPTION: SEQ ID NO:1:

```
GGGAGACGGC  GCTAGTGGGG  AGAGCGACCA  AGAGGCCCCC  TCCCCTCCCC  GGGTCCCCTT          60

CCCCTATCCC  CCTCCCCCCA  GCCTCCTTGC  CAACGCCCCC  TTTCCCTCTC  CCCCTCCCGC         120

TCGGCGCTGA  CCCCCCATCC  CCACCCCCGT  GGGAACACTG  GGAGCCTGCA  CTCCACAGAC         180

CCTCTCCTTG  CCTCTTCCCT  CACCTCAGCC  TCCGCTCCCC  GCCCTCTTCC  CGGCCCAGGG         240

CGCCGGCCCA  CCCTTCCCTC  CGCCGCCCCC  CGGCCGCGGG  GAGGAC ATG GCC GCG            295
                                                       Met Ala Ala
                                                        1

CAC AGG CCG GTG GAA TGG GTC CAG GCC GTG GTC AGC CGC TTC GAC GAG              343
His Arg Pro Val Glu Trp Val Gln Ala Val Val Ser Arg Phe Asp Glu
     5                  10                  15

CAG CTT CCA ATA AAA ACA GGA CAG CAG AAC ACA CAT ACC AAA GTC AGT              391
Gln Leu Pro Ile Lys Thr Gly Gln Gln Asn Thr His Thr Lys Val Ser
 20                  25                  30                  35
```

| | | | | | | | | | | | | | | | | |
|---|---|---|---|---|---|---|---|---|---|---|---|---|---|---|---|---|
| ACT | GAG | CAC | AAC | AAG | GAA | TGT | CTA | ATC | AAT | ATT | TCC | AAA | TAC | AAG | TTT | 439 |
| Thr | Glu | His | Asn | Lys | Glu | Cys | Leu | Ile | Asn | Ile | Ser | Lys | Tyr | Lys | Phe | |
| | | | | 40 | | | | | 45 | | | | | 50 | | |
| TCT | TTG | GTT | ATA | AGC | GGC | CTC | ACT | ACT | ATT | TTA | AAG | AAT | GTT | AAC | AAT | 487 |
| Ser | Leu | Val | Ile | Ser | Gly | Leu | Thr | Thr | Ile | Leu | Lys | Asn | Val | Asn | Asn | |
| | | | 55 | | | | | 60 | | | | | 65 | | | |
| ATG | AGA | ATA | TTT | GGA | GAA | GCT | GCT | GAA | AAA | AAT | TTA | TAT | CTC | TCT | CAG | 535 |
| Met | Arg | Ile | Phe | Gly | Glu | Ala | Ala | Glu | Lys | Asn | Leu | Tyr | Leu | Ser | Gln | |
| | | 70 | | | | | 75 | | | | | 80 | | | | |
| TTG | ATT | ATA | TTG | GAT | ACA | CTG | GAA | AAA | TGT | CTT | GCT | GGG | CAA | CCA | AAG | 583 |
| Leu | Ile | Ile | Leu | Asp | Thr | Leu | Glu | Lys | Cys | Leu | Ala | Gly | Gln | Pro | Lys | |
| | 85 | | | | | 90 | | | | | 95 | | | | | |
| GAC | ACA | ATG | AGA | TTA | GAT | GAA | ACG | ATG | CTG | GTC | AAA | CAG | TTG | CTG | CCA | 631 |
| Asp | Thr | Met | Arg | Leu | Asp | Glu | Thr | Met | Leu | Val | Lys | Gln | Leu | Leu | Pro | |
| 100 | | | | | 105 | | | | | 110 | | | | | 115 | |
| GAA | ATC | TGC | CAT | TTT | CTT | CAC | ACC | TGT | CGT | GAA | GGA | AAC | CAG | CAT | GCA | 679 |
| Glu | Ile | Cys | His | Phe | Leu | His | Thr | Cys | Arg | Glu | Gly | Asn | Gln | His | Ala | |
| | | | | 120 | | | | | 125 | | | | | 130 | | |
| GCT | GAA | CTT | CGG | AAT | TCT | GCC | TCT | GGG | GTT | TTA | TTT | TCT | CTC | AGC | TGC | 727 |
| Ala | Glu | Leu | Arg | Asn | Ser | Ala | Ser | Gly | Val | Leu | Phe | Ser | Leu | Ser | Cys | |
| | | | 135 | | | | | 140 | | | | | 145 | | | |
| AAC | AAC | TTC | AAT | GCA | GTC | TTT | AGT | CGC | ATT | TCT | ACC | AGG | TTA | CAG | GAA | 775 |
| Asn | Asn | Phe | Asn | Ala | Val | Phe | Ser | Arg | Ile | Ser | Thr | Arg | Leu | Gln | Glu | |
| | | 150 | | | | | 155 | | | | | 160 | | | | |
| TTA | ACT | GTT | TGT | TCA | GAA | GAC | AAT | GTT | GAT | GTT | CAT | GAT | ATA | GAA | TTG | 823 |
| Leu | Thr | Val | Cys | Ser | Glu | Asp | Asn | Val | Asp | Val | His | Asp | Ile | Glu | Leu | |
| | 165 | | | | | 170 | | | | | 175 | | | | | |
| TTA | CAG | TAT | ATC | AAT | GTG | GAT | TGT | GCA | AAA | TTA | AAA | CGA | CTC | CTG | AAG | 871 |
| Leu | Gln | Tyr | Ile | Asn | Val | Asp | Cys | Ala | Lys | Leu | Lys | Arg | Leu | Leu | Lys | |
| 180 | | | | | 185 | | | | | 190 | | | | | 195 | |
| GAA | ACA | GCA | TTT | AAA | TTT | AAA | GCC | CTA | AAG | AAG | GTT | GCG | CAG | TTA | GCA | 919 |
| Glu | Thr | Ala | Phe | Lys | Phe | Lys | Ala | Leu | Lys | Lys | Val | Ala | Gln | Leu | Ala | |
| | | | | 200 | | | | | 205 | | | | | 210 | | |
| GTT | ATA | AAT | AGC | CTG | GAA | AAG | GCA | TTT | TGG | AAC | TGG | GTA | GAA | AAT | TAT | 967 |
| Val | Ile | Asn | Ser | Leu | Glu | Lys | Ala | Phe | Trp | Asn | Trp | Val | Glu | Asn | Tyr | |
| | | | 215 | | | | | 220 | | | | | 225 | | | |
| CCA | GAT | GAA | TTT | ACA | AAA | CTA | TAC | CAG | ATC | CCA | CAG | ACT | GAT | ATG | GCT | 1015 |
| Pro | Asp | Glu | Phe | Thr | Lys | Leu | Tyr | Gln | Ile | Pro | Gln | Thr | Asp | Met | Ala | |
| | | 230 | | | | | 235 | | | | | 240 | | | | |
| GAA | TGT | GCA | GAA | AAG | CTA | TTT | GAC | TTG | GTG | GAT | GGT | TTT | GCT | GAA | AGC | 1063 |
| Glu | Cys | Ala | Glu | Lys | Leu | Phe | Asp | Leu | Val | Asp | Gly | Phe | Ala | Glu | Ser | |
| 245 | | | | | 250 | | | | | 255 | | | | | | |
| ACC | AAA | CGT | AAA | GCA | GCA | GTT | TGG | CCA | CTA | CAA | ATC | ATT | CTC | CTT | ATC | 1111 |
| Thr | Lys | Arg | Lys | Ala | Ala | Val | Trp | Pro | Leu | Gln | Ile | Ile | Leu | Leu | Ile | |
| 260 | | | | | 265 | | | | | 270 | | | | | 275 | |
| TTG | TGT | CCA | GAA | ATA | ATC | CAG | GAT | ATA | TCC | AAA | GAC | GTG | GTT | GAT | GAA | 1159 |
| Leu | Cys | Pro | Glu | Ile | Ile | Gln | Asp | Ile | Ser | Lys | Asp | Val | Val | Asp | Glu | |
| | | | | 280 | | | | | 285 | | | | | 290 | | |
| AAC | AAC | ATG | AAT | AAG | AAG | TTA | TTT | CTG | GAC | AGT | CTA | CGA | AAA | GCT | CTT | 1207 |
| Asn | Asn | Met | Asn | Lys | Lys | Leu | Phe | Leu | Asp | Ser | Leu | Arg | Lys | Ala | Leu | |
| | | | 295 | | | | | 300 | | | | | 305 | | | |
| GCT | GGC | CAT | GGA | GGA | AGT | AGG | CAG | CTG | ACA | GAA | AGT | GCT | GCA | ATT | GCC | 1255 |
| Ala | Gly | His | Gly | Gly | Ser | Arg | Gln | Leu | Thr | Glu | Ser | Ala | Ala | Ile | Ala | |
| | | 310 | | | | | 315 | | | | | 320 | | | | |
| TGT | GTC | AAA | CTG | TGT | AAA | GCA | AGT | ACT | TAC | ATC | AAT | TGG | GAA | GAT | AAC | 1303 |
| Cys | Val | Lys | Leu | Cys | Lys | Ala | Ser | Thr | Tyr | Ile | Asn | Trp | Glu | Asp | Asn | |
| | 325 | | | | | 330 | | | | | 335 | | | | | |
| TCT | GTC | ATT | TTC | CTA | CTT | GTT | CAG | TCC | ATG | GTG | GTT | GAT | CTT | AAG | AAC | 1351 |
| Ser | Val | Ile | Phe | Leu | Leu | Val | Gln | Ser | Met | Val | Val | Asp | Leu | Lys | Asn | |
| 340 | | | | | 345 | | | | | 350 | | | | | 355 | |

| | | | | | | | | | | | | | | | | |
|---|---|---|---|---|---|---|---|---|---|---|---|---|---|---|---|---|
| CTG | CTT | TTT | AAT | CCA | AGT | AAG | CCA | TTC | TCA | AGA | GGC | AGT | CAG | CCT | GCA | 1399 |
| Leu | Leu | Phe | Asn | Pro 360 | Ser | Lys | Pro | Phe 365 | Ser | Arg | Gly | Ser | Gln | Pro 370 | Ala | |
| GAT | GTG | GAT | CTA | ATG | ATT | GAC | TGC | CTT | GTT | TCT | TGC | TTT | CGT | ATA | AGC | 1447 |
| Asp | Val | Asp | Leu 375 | Met | Ile | Asp | Cys | Leu 380 | Val | Ser | Cys | Phe | Arg 385 | Ile | Ser | |
| CCT | CAC | AAC | AAC | CAA | CAC | TTT | AAG | ATC | TGC | CTG | GCT | CAG | AAT | TCA | CCT | 1495 |
| Pro | His | Asn 390 | Asn | Gln | His | Phe | Lys 395 | Ile | Cys | Leu | Ala | Gln 400 | Asn | Ser | Pro | |
| TCT | ACA | TTT | CAC | TAT | GTG | CTG | GTA | AAT | TCA | CTC | CAT | CGA | ATC | ATC | ACC | 1543 |
| Ser | Thr 405 | Phe | His | Tyr | Val | Leu 410 | Val | Asn | Ser | Leu | His 415 | Arg | Ile | Ile | Thr | |
| AAT | TCC | GCA | TTG | GAT | TGG | TGG | CCT | AAG | ATT | GAT | GCT | GTG | TAT | TGT | CAC | 1591 |
| Asn 420 | Ser | Ala | Leu | Asp | Trp 425 | Trp | Pro | Lys | Ile | Asp 430 | Ala | Val | Tyr | Cys | His 435 | |
| TCG | GTT | GAA | CTT | CGA | AAT | ATG | TTT | GGT | GAA | ACA | CTT | CAT | AAA | GCA | GTG | 1639 |
| Ser | Val | Glu | Leu | Arg 440 | Asn | Met | Phe | Gly | Glu 445 | Thr | Leu | His | Lys | Ala 450 | Val | |
| CAA | GGT | TGT | GGA | GCA | CAC | CCA | GCA | ATA | CGA | ATG | GCC | CCG | AGT | CTT | ACA | 1687 |
| Gln | Gly | Cys | Gly 455 | Ala | His | Pro | Ala | Ile 460 | Arg | Met | Ala | Pro | Ser 465 | Leu | Thr | |
| TTT | AAA | GAA | AAA | GTA | ACA | AGC | CTT | AAA | TTT | AAA | GAA | AAA | CCT | ACA | GAC | 1735 |
| Phe | Lys | Glu 470 | Lys | Val | Thr | Ser | Leu 475 | Lys | Phe | Lys | Glu | Lys 480 | Pro | Thr | Asp | |
| CTG | GAG | ACA | AGA | AGC | TAT | AAG | TAT | CTT | CTC | TTG | TCC | ATA | GTG | AAA | CTA | 1783 |
| Leu | Glu | Thr 485 | Arg | Ser | Tyr | Lys | Tyr 490 | Leu | Leu | Leu | Ser | Ile 495 | Val | Lys | Leu | |
| ATT | CAT | GCA | GAT | CCA | AAG | CTC | TTG | CTT | TGT | AAT | CCA | AGA | AAA | CAG | GGG | 1831 |
| Ile | His | Ala | Asp 500 | Pro | Lys | Leu | Leu 505 | Leu | Cys | Asn | Pro | Arg 510 | Lys | Gln | Gly 515 | |
| CCC | GAA | ACC | CAA | GGC | AGT | ACA | GCA | GAA | TTA | ATT | ACA | GGG | CTC | GTC | CAA | 1879 |
| Pro | Glu | Thr | Gln | Gly 520 | Ser | Thr | Ala | Glu | Leu 525 | Ile | Thr | Gly | Leu | Val 530 | Gln | |
| CTG | GTC | CCT | CAG | TCA | CAC | ATG | CCA | GAG | ATT | GCT | CAG | GAA | GCA | ATG | GAG | 1927 |
| Leu | Val | Pro | Gln | Ser 535 | His | Met | Pro | Glu 540 | Ile | Ala | Gln | Glu | Ala 545 | Met | Glu | |
| GCT | CTG | CTG | GTT | CTT | CAT | CAG | TTA | GAT | AGC | ATT | GAT | TTG | TGG | AAT | CCT | 1975 |
| Ala | Leu | Leu 550 | Val | Leu | His | Gln | Leu 555 | Asp | Ser | Ile | Asp | Leu 560 | Trp | Asn | Pro | |
| GAT | GCT | CCT | GTA | GAA | ACA | TTT | TGG | GAG | ATT | AGC | TCA | CAA | ATG | CTT | TTT | 2023 |
| Asp | Ala | Pro 565 | Val | Glu | Thr | Phe | Trp 570 | Glu | Ile | Ser | Ser | Gln 575 | Met | Leu | Phe | |
| TAC | ATC | TGC | AAG | AAA | TTA | ACT | AGT | CAT | CAA | ATG | CTT | AGT | AGC | ACA | GAA | 2071 |
| Tyr | Ile | Cys | Lys 580 | Lys | Leu | Thr | Ser | His 585 | Gln | Met | Leu | Ser | Ser 590 | Thr | Glu 595 | |
| ATT | CTC | AAG | TGG | TTG | CGG | GAA | ATA | TTG | ATC | TGC | AGG | AAT | AAA | TTT | CTT | 2119 |
| Ile | Leu | Lys | Trp | Leu 600 | Arg | Glu | Ile | Leu | Ile 605 | Cys | Arg | Asn | Lys | Phe 610 | Leu | |
| CTT | AAA | AAT | AAG | CAG | GCA | GAT | AGA | AGT | TCC | TGT | CAC | TTT | CTC | CTT | TTT | 2167 |
| Leu | Lys | Asn | Lys 615 | Gln | Ala | Asp | Arg | Ser 620 | Ser | Cys | His | Phe 625 | Leu | Leu | Phe | |
| TAC | GGG | GTA | GGA | TGT | GAT | ATT | CCT | TCT | AGT | GGA | AAT | ACC | AGT | CAA | ATG | 2215 |
| Tyr | Gly | Val 630 | Gly | Cys | Asp | Ile | Pro | Ser 635 | Ser | Gly | Asn | Thr 640 | Ser | Gln | Met | |
| TCC | ATG | GAT | CAT | GAA | GAA | TTA | CTA | CGT | ACT | CCT | GGA | GCC | TCT | CTC | CGG | 2263 |
| Ser | Met | Asp | His 645 | Glu | Glu | Leu | Leu 650 | Arg | Thr | Pro | Gly 655 | Ala | Ser | Leu | Arg | |
| AAG | GGA | AAA | GGG | AAC | TCC | TCT | ATG | GAT | AGT | GCA | GCA | GGA | TGC | AGC | GGA | 2311 |
| Lys | Gly 660 | Lys | Gly | Asn | Ser 665 | Ser | Met | Asp | Ser 670 | Ala | Ala | Gly | Cys | Ser | Gly 675 | |

| | | | | | | | | | | | | | | | |
|---|---|---|---|---|---|---|---|---|---|---|---|---|---|---|---|
| ACC | CCC | CCG | ATT | TGC | CGA | CAA | GCC | CAG | ACC | AAA | CTA | GAA | GTG | GCC | CTG | 2359
| Thr | Pro | Pro | Ile | Cys | Arg | Gln | Ala | Gln | Thr | Lys | Leu | Glu | Val | Ala | Leu |
| | | | | 680 | | | | | 685 | | | | | | 690 |
| TAC | ATG | TTT | CTG | TGG | AAC | CCT | GAC | ACT | GAA | GCT | GTT | CTG | GTT | GCC | ATG | 2407
| Tyr | Met | Phe | Leu | Trp | Asn | Pro | Asp | Thr | Glu | Ala | Val | Leu | Val | Ala | Met |
| | | | | 695 | | | | | 700 | | | | | | 705 |
| TCC | TGT | TTC | CGC | CAC | CTC | TGT | GAG | GAA | GCA | GAT | ATC | CGG | TGT | GGG | GTG | 2455
| Ser | Cys | Phe | Arg | His | Leu | Cys | Glu | Glu | Ala | Asp | Ile | Arg | Cys | Gly | Val |
| | | 710 | | | | | 715 | | | | | 720 | | | |
| GAT | GAA | GTG | TCA | GTG | CAT | AAC | CTC | TTG | CCC | AAC | TAT | AAC | ACA | TTC | ATG | 2503
| Asp | Glu | Val | Ser | Val | His | Asn | Leu | Leu | Pro | Asn | Tyr | Asn | Thr | Phe | Met |
| | 725 | | | | | 730 | | | | | 735 | | | | |
| GAG | TTT | GCC | TCT | GTC | AGC | AAT | ATG | ATG | TCA | ACA | GGA | AGA | GCA | GCA | CTT | 2551
| Glu | Phe | Ala | Ser | Val | Ser | Asn | Met | Met | Ser | Thr | Gly | Arg | Ala | Ala | Leu |
| 740 | | | | | 745 | | | | | 750 | | | | | 755 |
| CAG | AAA | AGA | GTG | ATG | GCA | CTG | CTG | AGG | CGC | ATT | GAG | CAT | CCC | ACT | GCA | 2599
| Gln | Lys | Arg | Val | Met | Ala | Leu | Leu | Arg | Arg | Ile | Glu | His | Pro | Thr | Ala |
| | | | | 760 | | | | | 765 | | | | | 770 | |
| GGA | AAC | ACT | GAG | GCT | TGG | GAA | GAT | ACA | CAT | GCA | AAA | TGG | GAA | CAA | GCA | 2647
| Gly | Asn | Thr | Glu | Ala | Trp | Glu | Asp | Thr | His | Ala | Lys | Trp | Glu | Gln | Ala |
| | | | 775 | | | | | 780 | | | | | 785 | | |
| ACA | AAG | CTA | ATC | CTT | AAC | TAT | CCA | AAA | GCC | AAA | ATG | GAA | GAT | GGC | CAG | 2695
| Thr | Lys | Leu | Ile | Leu | Asn | Tyr | Pro | Lys | Ala | Lys | Met | Glu | Asp | Gly | Gln |
| | | 790 | | | | | 795 | | | | | 800 | | | |
| GCT | GCT | GAA | AGC | CTT | CAC | AAG | ACC | ATT | GTT | AAG | AGG | CGA | ATG | TCC | CAT | 2743
| Ala | Ala | Glu | Ser | Leu | His | Lys | Thr | Ile | Val | Lys | Arg | Arg | Met | Ser | His |
| | 805 | | | | | 810 | | | | | 815 | | | | |
| GTG | AGT | GGA | GGA | GGA | TCC | ATA | GAT | TTG | TCT | GAC | ACA | GAC | TCC | CTA | CAG | 2791
| Val | Ser | Gly | Gly | Gly | Ser | Ile | Asp | Leu | Ser | Asp | Thr | Asp | Ser | Leu | Gln |
| 820 | | | | | 825 | | | | | 830 | | | | | 835 |
| GAA | TGG | ATC | AAC | ATG | ACT | GGC | TTC | CTT | TGT | GCC | CTT | GGA | GGA | GTG | TGC | 2839
| Glu | Trp | Ile | Asn | Met | Thr | Gly | Phe | Leu | Cys | Ala | Leu | Gly | Gly | Val | Cys |
| | | | | 840 | | | | | 845 | | | | | 850 | |
| CTC | CAG | CAG | AGA | AGC | AAT | TCT | GGC | CTG | GCA | ACC | TAT | AGC | CCA | CCC | ATG | 2887
| Leu | Gln | Gln | Arg | Ser | Asn | Ser | Gly | Leu | Ala | Thr | Tyr | Ser | Pro | Pro | Met |
| | | | 855 | | | | | 860 | | | | | 865 | | |
| GGT | CCA | GTC | AGT | GAA | CGT | AAG | GGT | TCT | ATG | ATT | TCA | GTG | ATG | TCT | TCA | 2935
| Gly | Pro | Val | Ser | Glu | Arg | Lys | Gly | Ser | Met | Ile | Ser | Val | Met | Ser | Ser |
| | | 870 | | | | | 875 | | | | | 880 | | | |
| GAG | GGA | AAC | GCA | GAT | ACA | CCT | GTC | AGC | AAA | TTT | ATG | GAT | CGG | CTG | TTG | 2983
| Glu | Gly | Asn | Ala | Asp | Thr | Pro | Val | Ser | Lys | Phe | Met | Asp | Arg | Leu | Leu |
| | 885 | | | | | 890 | | | | | 895 | | | | |
| TCC | TTA | ATG | GTG | TGT | AAC | CAT | GAG | AAA | GTG | GGA | CTT | CAA | ATA | CGG | ACC | 3031
| Ser | Leu | Met | Val | Cys | Asn | His | Glu | Lys | Val | Gly | Leu | Gln | Ile | Arg | Thr |
| 900 | | | | | 905 | | | | | 910 | | | | | 915 |
| AAT | GTT | AAG | GAT | CTG | GTG | GGT | CTA | GAA | TTG | AGT | CCT | GCT | CTG | TAT | CCA | 3079
| Asn | Val | Lys | Asp | Leu | Val | Gly | Leu | Glu | Leu | Ser | Pro | Ala | Leu | Tyr | Pro |
| | | | | 920 | | | | | 925 | | | | | 930 | |
| ATG | CTA | TTT | AAC | AAA | TTG | AAG | AAT | ACC | ATC | AGC | AAG | TTT | TTT | GAC | TCC | 3127
| Met | Leu | Phe | Asn | Lys | Leu | Lys | Asn | Thr | Ile | Ser | Lys | Phe | Phe | Asp | Ser |
| | | | 935 | | | | | 940 | | | | | 945 | | |
| CAA | GGA | CAG | GTT | TTA | TTG | ACT | GAT | ACC | AAT | ACT | CAA | TTT | GTA | GAA | CAA | 3175
| Gln | Gly | Gln | Val | Leu | Leu | Thr | Asp | Thr | Asn | Thr | Gln | Phe | Val | Glu | Gln |
| | | 950 | | | | | 955 | | | | | 960 | | | |
| ACC | ATA | GCT | ATA | ATG | AAG | AAC | TTG | CTA | GAT | AAT | CAT | ACT | GAA | GGC | AGC | 3223
| Thr | Ile | Ala | Ile | Met | Lys | Asn | Leu | Leu | Asp | Asn | His | Thr | Glu | Gly | Ser |
| | 965 | | | | | 970 | | | | | 975 | | | | |
| TCT | GAA | CAT | CTA | GGG | CAA | GCT | AGC | ATT | GAA | ACA | ATG | ATG | TTA | AAT | CTG | 3271
| Ser | Glu | His | Leu | Gly | Gln | Ala | Ser | Ile | Glu | Thr | Met | Met | Leu | Asn | Leu |
| 980 | | | | | 985 | | | | | 990 | | | | | 995 |

```
GTC AGG TAT GTT CGT GTG CTT GGG AAT ATG GTC CAT GCA ATT CAA ATA      3319
Val Arg Tyr Val Arg Val Leu Gly Asn Met Val His Ala Ile Gln Ile
            1000                1005                1010

AAA ACG AAA CTG TGT CAA TTA GTT GAA GTA ATG ATG GCA AGG AGA GAT      3367
Lys Thr Lys Leu Cys Gln Leu Val Glu Val Met Met Ala Arg Arg Asp
            1015                1020                1025

GAC CTC TCA TTT TGC CAA GAG ATG AAA TTT AGG AAT AAG ATG GTA GAA      3415
Asp Leu Ser Phe Cys Gln Glu Met Lys Phe Arg Asn Lys Met Val Glu
            1030                1035                1040

TAC CTG ACA GAC TGG GTT ATG GGA ACA TCA AAC CAA GCA GCA GAT GAT      3463
Tyr Leu Thr Asp Trp Val Met Gly Thr Ser Asn Gln Ala Ala Asp Asp
            1045                1050                1055

GAT GTA AAA TGT CTT ACA AGA GAT TTG GAC CAG GCA AGC ATG GAA GCA      3511
Asp Val Lys Cys Leu Thr Arg Asp Leu Asp Gln Ala Ser Met Glu Ala
1060            1065                1070                1075

GTA GTT TCA CTT CTA GCT GGT CTC CCT CTG CAG CCT GAA GAA GGA GAT      3559
Val Val Ser Leu Leu Ala Gly Leu Pro Leu Gln Pro Glu Glu Gly Asp
                1080                1085                1090

GGT GTG GAA TTG ATG GAA GCC AAA TCA CAG TTA TTT CTT AAA TAC TTC      3607
Gly Val Glu Leu Met Glu Ala Lys Ser Gln Leu Phe Leu Lys Tyr Phe
            1095                1100                1105

ACA TTA TTT ATG AAC CTT TTG AAT GAC TGC AGT GAA GTT GAA GAT GAA      3655
Thr Leu Phe Met Asn Leu Leu Asn Asp Cys Ser Glu Val Glu Asp Glu
            1110                1115                1120

AGT GCG CAA ACA GGT GGC AGG AAA CGT GGC ATG TCT CGG AGG CTG GCA      3703
Ser Ala Gln Thr Gly Gly Arg Lys Arg Gly Met Ser Arg Arg Leu Ala
            1125                1130                1135

TCA CTG AGG CAC TGT ACG GTC CTT GCA ATG TCA AAC TTA CTC AAT GCC      3751
Ser Leu Arg His Cys Thr Val Leu Ala Met Ser Asn Leu Leu Asn Ala
1140            1145                1150                1155

AAC GTA GAC AGT GGT CTC ATG CAC TCC ATA GGC TTA GGT TAC CAC AAG      3799
Asn Val Asp Ser Gly Leu Met His Ser Ile Gly Leu Gly Tyr His Lys
                1160                1165                1170

GAT CTC CAG ACA AGA GCT ACA TTT ATG GAA GTT CTG ACA AAA ATC CTT      3847
Asp Leu Gln Thr Arg Ala Thr Phe Met Glu Val Leu Thr Lys Ile Leu
            1175                1180                1185

CAA CAA GGC ACA GAA TTT GAC ACA CTT GCA GAA ACA GTA TTG GCT GAT      3895
Gln Gln Gly Thr Glu Phe Asp Thr Leu Ala Glu Thr Val Leu Ala Asp
            1190                1195                1200

CGG TTT GAG AGA TTG GTG GAA CTG GTC ACA ATG ATG GGT GAT CAA GGA      3943
Arg Phe Glu Arg Leu Val Glu Leu Val Thr Met Met Gly Asp Gln Gly
            1205                1210                1215

GAA CTC CCT ATA GCG ATG GCT CTG GCC AAT GTG GTT CCT TGT TCT CAG      3991
Glu Leu Pro Ile Ala Met Ala Leu Ala Asn Val Val Pro Cys Ser Gln
1220                1225                1230                1235

TGG GAT GAA CTA GCT CGA GTT CTG GTT ACT CTG TTT GAT TCT CGG CAT      4039
Trp Asp Glu Leu Ala Arg Val Leu Val Thr Leu Phe Asp Ser Arg His
            1240                1245                1250

TTA CTC TAC CAA CTG CTC TGG AAC ATG TTT TCT AAA GAA GTA GAA TTG      4087
Leu Leu Tyr Gln Leu Leu Trp Asn Met Phe Ser Lys Glu Val Glu Leu
            1255                1260                1265

GCA GAC TCC ATG CAG ACT CTC TTC CGA GGC AAC AGC TTG GCC AGT AAA      4135
Ala Asp Ser Met Gln Thr Leu Phe Arg Gly Asn Ser Leu Ala Ser Lys
            1270                1275                1280

ATA ATG ACA TTC TGT TTC AAG GTA TAT GGT GCT ACC TAT CTA CAA AAA      4183
Ile Met Thr Phe Cys Phe Lys Val Tyr Gly Ala Thr Tyr Leu Gln Lys
            1285                1290                1295

CTC CTG GAT CCT TTA TTA CGA ATT GTG ATC ACA TCC TCT GAT TGG CAA      4231
Leu Leu Asp Pro Leu Leu Arg Ile Val Ile Thr Ser Ser Asp Trp Gln
1300                1305                1310                1315
```

| | | | | | | | | | | | | | | | | |
|---|---|---|---|---|---|---|---|---|---|---|---|---|---|---|---|---|
| CAT | GTT | AGC | TTT | GAA | GTG | GAT | CCT | ACC | AGG | TTA | GAA | CCA | TCA | GAG | AGC | 4279 |
| His | Val | Ser | Phe | Glu | Val | Asp | Pro | Thr | Arg | Leu | Glu | Pro | Ser | Glu | Ser | |
| | | | 1320 | | | | 1325 | | | | | 1330 | | | | |
| CTT | GAG | GAA | AAC | CAG | CGG | AAC | CTC | CTT | CAG | ATG | ACT | GAA | AAG | TTC | TTC | 4327 |
| Leu | Glu | Glu | Asn | Gln | Arg | Asn | Leu | Leu | Gln | Met | Thr | Glu | Lys | Phe | Phe | |
| | | | | 1335 | | | | 1340 | | | | | 1345 | | | |
| CAT | GCC | ATC | ATC | AGT | TCC | TCC | TCA | GAA | TTC | CCC | CCT | CAA | CTT | CGA | AGT | 4375 |
| His | Ala | Ile | Ile | Ser | Ser | Ser | Ser | Glu | Phe | Pro | Pro | Gln | Leu | Arg | Ser | |
| | | 1350 | | | | | 1355 | | | | | 1360 | | | | |
| GTG | TGC | CAC | TGT | TTA | TAC | CAG | GTG | GTT | AGC | CAG | CGT | TTC | CCT | CAG | AAC | 4423 |
| Val | Cys | His | Cys | Leu | Tyr | Gln | Val | Val | Ser | Gln | Arg | Phe | Pro | Gln | Asn | |
| | | 1365 | | | | | 1370 | | | | | 1375 | | | | |
| AGC | ATC | GGT | GCA | GTA | GGA | AGT | GCC | ATG | TTC | CTC | AGA | TTT | ATC | AAT | CCT | 4471 |
| Ser | Ile | Gly | Ala | Val | Gly | Ser | Ala | Met | Phe | Leu | Arg | Phe | Ile | Asn | Pro | |
| 1380 | | | | | 1385 | | | | | 1390 | | | | | 1395 | |
| GCC | ATT | GTC | TCA | CCG | TAT | GAA | GCA | GGG | ATT | TTA | GAT | AAA | AAG | CCA | CCA | 4519 |
| Ala | Ile | Val | Ser | Pro | Tyr | Glu | Ala | Gly | Ile | Leu | Asp | Lys | Lys | Pro | Pro | |
| | | | | 1400 | | | | | 1405 | | | | | 1410 | | |
| CCT | AGA | ATC | GAA | AGG | GGC | TTG | AAG | TTA | ATG | TCA | AAG | ATA | CTT | CAG | AGT | 4567 |
| Pro | Arg | Ile | Glu | Arg | Gly | Leu | Lys | Leu | Met | Ser | Lys | Ile | Leu | Gln | Ser | |
| | | | 1415 | | | | | 1420 | | | | | 1425 | | | |
| ATT | GCC | AAT | CAT | GTT | CTC | TTC | ACA | AAA | GAA | GAA | CAT | ATG | CGG | CCT | TTC | 4615 |
| Ile | Ala | Asn | His | Val | Leu | Phe | Thr | Lys | Glu | Glu | His | Met | Arg | Pro | Phe | |
| | | | 1430 | | | | | 1435 | | | | | 1440 | | | |
| AAT | GAT | TTT | GTG | AAA | AGC | AAC | TTT | GAT | GCA | GCA | CGC | AGG | TTT | TTC | CTT | 4663 |
| Asn | Asp | Phe | Val | Lys | Ser | Asn | Phe | Asp | Ala | Ala | Arg | Arg | Phe | Phe | Leu | |
| | | | 1445 | | | | | 1450 | | | | | 1455 | | | |
| GAT | ATA | GCA | TCT | GAT | TGT | CCT | ACA | AGT | GAT | GCA | GTA | AAT | CAT | AGT | CTT | 4711 |
| Asp | Ile | Ala | Ser | Asp | Cys | Pro | Thr | Ser | Asp | Ala | Val | Asn | His | Ser | Leu | |
| 1460 | | | | | 1465 | | | | | 1470 | | | | | 1475 | |
| TCC | TTC | ATA | AGT | GAC | GGC | AAT | GTG | CTT | GCT | TTA | CAT | CGT | CTA | CTC | TGG | 4759 |
| Ser | Phe | Ile | Ser | Asp | Gly | Asn | Val | Leu | Ala | Leu | His | Arg | Leu | Leu | Trp | |
| | | | | 1480 | | | | | 1485 | | | | | 1490 | | |
| AAC | AAT | CAG | GAG | AAA | ATT | GGG | CAG | TAT | CTT | TCC | AGC | AAC | AGG | GAT | CAT | 4807 |
| Asn | Asn | Gln | Glu | Lys | Ile | Gly | Gln | Tyr | Leu | Ser | Ser | Asn | Arg | Asp | His | |
| | | | | 1495 | | | | | 1500 | | | | | 1505 | | |
| AAA | GCT | GTT | GGA | AGA | CGA | CCT | TTT | GAT | AAG | ATG | GCA | ACA | CTT | CTT | GCA | 4855 |
| Lys | Ala | Val | Gly | Arg | Arg | Pro | Phe | Asp | Lys | Met | Ala | Thr | Leu | Leu | Ala | |
| | | | 1510 | | | | | 1515 | | | | | 1520 | | | |
| TAC | CTG | GGT | CCT | CCA | GAG | CAC | AAA | CCT | GTG | GCA | GAT | ACA | CAC | TGG | TCC | 4903 |
| Tyr | Leu | Gly | Pro | Pro | Glu | His | Lys | Pro | Val | Ala | Asp | Thr | His | Trp | Ser | |
| | 1525 | | | | | 1530 | | | | | 1535 | | | | | |
| AGC | CTT | AAC | CTT | ACC | AGT | TCA | AAG | TTT | GAG | GAA | TTT | ATG | ACT | AGG | CAT | 4951 |
| Ser | Leu | Asn | Leu | Thr | Ser | Ser | Lys | Phe | Glu | Glu | Phe | Met | Thr | Arg | His | |
| 1540 | | | | | 1545 | | | | | 1550 | | | | | 1555 | |
| CAG | GTA | CAT | GAA | AAA | GAA | GAA | TTC | AAG | GCT | TTG | AAA | ACG | TTA | AGT | ATT | 4999 |
| Gln | Val | His | Glu | Lys | Glu | Glu | Phe | Lys | Ala | Leu | Lys | Thr | Leu | Ser | Ile | |
| | | | | 1560 | | | | | 1565 | | | | | 1570 | | |
| TTC | TAC | CAA | GCT | GGG | ACT | TCC | AAA | GCT | GGG | AAT | CCT | ATT | TTT | TAT | TAT | 5047 |
| Phe | Tyr | Gln | Ala | Gly | Thr | Ser | Lys | Ala | Gly | Asn | Pro | Ile | Phe | Tyr | Tyr | |
| | | | 1575 | | | | | 1580 | | | | | 1585 | | | |
| GTT | GCA | CGG | AGG | TTC | AAA | ACT | GGT | CAA | ATC | AAT | GGT | GAT | TTG | CTG | ATA | 5095 |
| Val | Ala | Arg | Arg | Phe | Lys | Thr | Gly | Gln | Ile | Asn | Gly | Asp | Leu | Leu | Ile | |
| | | 1590 | | | | | 1595 | | | | | 1600 | | | | |
| TAC | CAT | GTC | TTA | CTG | ACT | TTA | AAG | CCA | TAT | TAT | GCA | AAG | CCA | TAT | GAA | 5143 |
| Tyr | His | Val | Leu | Leu | Thr | Leu | Lys | Pro | Tyr | Tyr | Ala | Lys | Pro | Tyr | Glu | |
| | 1605 | | | | | 1610 | | | | | 1615 | | | | | |
| ATT | GTA | GTG | GAC | CTT | ACC | CAT | ACC | GGG | CCT | AGC | AAT | CGC | TTT | AAA | ACA | 5191 |
| Ile | Val | Val | Asp | Leu | Thr | His | Thr | Gly | Pro | Ser | Asn | Arg | Phe | Lys | Thr | |
| 1620 | | | | | 1625 | | | | | 1630 | | | | | 1635 | |

```
GAC  TTT  CTC  TCT  AAG  TGG  TTT  GTT  GTT  TTT  CCT  GGC  TTT  GCT  TAC  GAC      5239
Asp  Phe  Leu  Ser  Lys  Trp  Phe  Val  Val  Phe  Pro  Gly  Phe  Ala  Tyr  Asp
               1640                     1645                          1650

AAC  GTC  TCC  GCA  GTC  TAT  ATC  TAT  AAC  TGT  AAC  TCC  TGG  GTC  AGG  GAG      5287
Asn  Val  Ser  Ala  Val  Tyr  Ile  Tyr  Asn  Cys  Asn  Ser  Trp  Val  Arg  Glu
               1655                     1660                          1665

TAC  ACC  AAG  TAT  CAT  GAG  CGG  CTG  CTG  ACT  GGC  CTC  AAA  GGT  AGC  AAA      5335
Tyr  Thr  Lys  Tyr  His  Glu  Arg  Leu  Leu  Thr  Gly  Leu  Lys  Gly  Ser  Lys
               1670                     1675                          1680

AGG  CTT  GTT  TTC  ATA  GAC  TGT  CCT  GGG  AAA  CTG  GCT  GAG  CAC  ATA  GAG      5383
Arg  Leu  Val  Phe  Ile  Asp  Cys  Pro  Gly  Lys  Leu  Ala  Glu  His  Ile  Glu
               1685                     1690                          1695

CAT  GAA  CAA  CAG  AAA  CTA  CCT  GCT  GCC  ACC  TTG  GCT  TTA  GAA  GAG  GAC      5431
His  Glu  Gln  Gln  Lys  Leu  Pro  Ala  Ala  Thr  Leu  Ala  Leu  Glu  Glu  Asp
1700                     1705                     1710                     1715

CTG  AAG  GTA  TTC  CAC  AAT  GCT  CTC  AAG  CTA  GCT  CAC  AAA  GAC  ACC  AAA      5479
Leu  Lys  Val  Phe  His  Asn  Ala  Leu  Lys  Leu  Ala  His  Lys  Asp  Thr  Lys
               1720                     1725                          1730

GTT  TCT  ATT  AAA  GTT  GGT  TCT  ACT  GCT  GTC  CAA  GTA  ACT  TCA  GCA  GAG      5527
Val  Ser  Ile  Lys  Val  Gly  Ser  Thr  Ala  Val  Gln  Val  Thr  Ser  Ala  Glu
               1735                     1740                          1745

CGA  ACA  AAA  GTC  CTA  GGG  CAA  TCA  GTC  TTT  CTA  AAT  GAC  ATT  TAT  TAT      5575
Arg  Thr  Lys  Val  Leu  Gly  Gln  Ser  Val  Phe  Leu  Asn  Asp  Ile  Tyr  Tyr
               1750                     1755                          1760

GCT  TCG  GAA  ATT  GAA  GAA  ATC  TGC  CTA  GTA  GAT  GAG  AAC  CAG  TTC  ACC      5623
Ala  Ser  Glu  Ile  Glu  Glu  Ile  Cys  Leu  Val  Asp  Glu  Asn  Gln  Phe  Thr
               1765                     1770                          1775

TTA  ACC  ATT  GCA  AAC  CAG  GGC  ACG  CCG  CTC  ACC  TTC  ATG  CAC  CAG  GAG      5671
Leu  Thr  Ile  Ala  Asn  Gln  Gly  Thr  Pro  Leu  Thr  Phe  Met  His  Gln  Glu
1780                     1785                     1790                     1795

TGT  GAA  GCC  ATT  GTC  CAG  TCT  ATC  ATT  CAT  ATC  CGG  ACC  CGC  TGG  GAA      5719
Cys  Glu  Ala  Ile  Val  Gln  Ser  Ile  Ile  His  Ile  Arg  Thr  Arg  Trp  Glu
               1800                     1805                          1810

CTG  TCA  CAG  CCC  GAC  TCT  ATC  CCC  CAA  CAC  ACC  AAG  ATT  CGG  CCA  AAA      5767
Leu  Ser  Gln  Pro  Asp  Ser  Ile  Pro  Gln  His  Thr  Lys  Ile  Arg  Pro  Lys
               1815                     1820                          1825

GAT  GTC  CCT  GGG  ACA  CTG  CTC  AAT  ATC  GCA  TTA  CTT  AAT  TTA  GGC  AGT      5815
Asp  Val  Pro  Gly  Thr  Leu  Leu  Asn  Ile  Ala  Leu  Leu  Asn  Leu  Gly  Ser
               1830                     1835                          1840

TCT  GAC  CCG  AGT  TTA  CGG  TCA  GCT  GCC  TAT  AAT  CTT  CTG  TGT  GCC  TTA      5863
Ser  Asp  Pro  Ser  Leu  Arg  Ser  Ala  Ala  Tyr  Asn  Leu  Leu  Cys  Ala  Leu
               1845                     1850                          1855

ACT  TGT  ACC  TTT  AAT  TTA  AAA  ATC  GAG  GGC  CAG  TTA  CTA  GAG  ACA  TCA      5911
Thr  Cys  Thr  Phe  Asn  Leu  Lys  Ile  Glu  Gly  Gln  Leu  Leu  Glu  Thr  Ser
1860                     1865                     1870                     1875

GGT  TTA  TGT  ATC  CCT  GCC  AAC  AAC  ACC  CTC  TTT  ATT  GTC  TCT  ATT  AGT      5959
Gly  Leu  Cys  Ile  Pro  Ala  Asn  Asn  Thr  Leu  Phe  Ile  Val  Ser  Ile  Ser
               1880                     1885                          1890

AAG  ACA  CTG  GCA  GCC  AAT  GAG  CCA  CAC  CTC  ACG  TTA  GAA  TTT  TTG  GAA      6007
Lys  Thr  Leu  Ala  Ala  Asn  Glu  Pro  His  Leu  Thr  Leu  Glu  Phe  Leu  Glu
               1895                     1900                          1905

GAG  TGT  ATT  TCT  GGA  TTT  AGC  AAA  TCT  AGT  ATT  GAA  TTG  AAA  CAC  CTT      6055
Glu  Cys  Ile  Ser  Gly  Phe  Ser  Lys  Ser  Ser  Ile  Glu  Leu  Lys  His  Leu
               1910                     1915                          1920

TGT  TTG  GAA  TAC  ATG  ACT  CCA  TGG  CTG  TCA  AAT  CTA  GTT  CGT  TTT  TGC      6103
Cys  Leu  Glu  Tyr  Met  Thr  Pro  Trp  Leu  Ser  Asn  Leu  Val  Arg  Phe  Cys
               1925                     1930                          1935

AAG  CAT  AAT  GAT  GAT  GCC  AAA  CGA  CAA  AGA  GTT  ACT  GCT  ATT  CTT  GAC      6151
Lys  His  Asn  Asp  Asp  Ala  Lys  Arg  Gln  Arg  Val  Thr  Ala  Ile  Leu  Asp
1940                     1945                     1950                     1955
```

```
AAG CTG ATA ACA ATG ACC ATC AAT GAA AAA CAG ATG TAC CCA TCT ATT    6199
Lys Leu Ile Thr Met Thr Ile Asn Glu Lys Gln Met Tyr Pro Ser Ile
            1960                1965                1970

CAA GCA AAA ATA TGG GGA AGC TTG GGA CAG ATT ACA GAT CTG CTT GAT    6247
Gln Ala Lys Ile Trp Gly Ser Leu Gly Gln Ile Thr Asp Leu Leu Asp
        1975                1980                1985

GTT GTA CTA GAC AGT TTC ATC AAA ACC AGT GCA ACA GGT GGC TTG GGA    6295
Val Val Leu Asp Ser Phe Ile Lys Thr Ser Ala Thr Gly Gly Leu Gly
            1990                1995                2000

TCA ATA AAA GCT GAG GTG ATG GCA GAT ACT GCT GTA GCT TTG GCT TCT    6343
Ser Ile Lys Ala Glu Val Met Ala Asp Thr Ala Val Ala Leu Ala Ser
        2005                2010                2015

GGA AAT GTG AAA TTG GTT TCA AGC AAG GTT ATT GGA AGG ATG TGC AAA    6391
Gly Asn Val Lys Leu Val Ser Ser Lys Val Ile Gly Arg Met Cys Lys
2020            2025                2030                    2035

ATA ATT GAC AAG ACA TGC TTA TCT CCA ACT CCT ACT TTA GAA CAA CAT    6439
Ile Ile Asp Lys Thr Cys Leu Ser Pro Thr Pro Thr Leu Glu Gln His
            2040                2045                2050

CTT ATG TGG GAT GAT ATT GCT ATT TTA GCA CGC TAC ATG CTG ATG CTG    6487
Leu Met Trp Asp Asp Ile Ala Ile Leu Ala Arg Tyr Met Leu Met Leu
        2055                2060                2065

TCC TTC AAC AAT TCC CTT GAT GTG GCA GCT CAT CTT CCC TAC CTC TTC    6535
Ser Phe Asn Asn Ser Leu Asp Val Ala Ala His Leu Pro Tyr Leu Phe
            2070                2075                2080

CAC GTT GTT ACT TTC TTA GTA GCC ACA GGT CCG CTC TCC CTT AGA GCT    6583
His Val Val Thr Phe Leu Val Ala Thr Gly Pro Leu Ser Leu Arg Ala
        2085                2090                2095

TCC ACA CAT GGA CTG GTC ATT AAT ATC ATT CAC TCT CTG TGT ACT TGT    6631
Ser Thr His Gly Leu Val Ile Asn Ile Ile His Ser Leu Cys Thr Cys
2100            2105                2110                    2115

TCA CAG CTT CAT TTT AGT GAA GAG ACC AAG CAA GTT TTG AGA CTC AGT    6679
Ser Gln Leu His Phe Ser Glu Glu Thr Lys Gln Val Leu Arg Leu Ser
            2120                2125                2130

CTG ACA GAG TTC TCA TTA CCC AAA TTT TAC TTG CTG TTT GGC ATT AGC    6727
Leu Thr Glu Phe Ser Leu Pro Lys Phe Tyr Leu Leu Phe Gly Ile Ser
        2135                2140                2145

AAA GTC AAG TCA GCT GCT GTC ATT GCC TTC CGT TCC AGT TAC CGG GAC    6775
Lys Val Lys Ser Ala Ala Val Ile Ala Phe Arg Ser Ser Tyr Arg Asp
            2150                2155                2160

AGG TCA TTC TCT CCT GGC TCC TAT GAG AGA GAG ACT TTT GCT TTG ACA    6823
Arg Ser Phe Ser Pro Gly Ser Tyr Glu Arg Glu Thr Phe Ala Leu Thr
        2165                2170                2175

TCC TTG GAA ACA GTC ACA GAA GCT TTG TTG GAG ATC ATG GAG GCA TGC    6871
Ser Leu Glu Thr Val Thr Glu Ala Leu Leu Glu Ile Met Glu Ala Cys
2180            2185                2190                    2195

ATG AGA GAT ATT CCA ACG TGC AAG TGG CTG GAC CAG TGG ACA GAA CTA    6919
Met Arg Asp Ile Pro Thr Cys Lys Trp Leu Asp Gln Trp Thr Glu Leu
            2200                2205                2210

GCT CAA AGA TTT GCA TTC CAA TAT AAT CCA TCC CTG CAA CCA AGA GCT    6967
Ala Gln Arg Phe Ala Phe Gln Tyr Asn Pro Ser Leu Gln Pro Arg Ala
        2215                2220                2225

CTT GTT GTC TTT GGG TGT ATT AGC AAA CGA GTG TCT CAT GGG CAG ATA    7015
Leu Val Val Phe Gly Cys Ile Ser Lys Arg Val Ser His Gly Gln Ile
            2230                2235                2240

AAG CAG ATA ATC CGT ATT CTT AGC AAG GCA CTT GAG AGT TGC TTA AAA    7063
Lys Gln Ile Ile Arg Ile Leu Ser Lys Ala Leu Glu Ser Cys Leu Lys
        2245                2250                2255

GGA CCT GAC ACT TAC AAC AGT CAA GTT CTG ATA GAA GCT ACA GTA ATA    7111
Gly Pro Asp Thr Tyr Asn Ser Gln Val Leu Ile Glu Ala Thr Val Ile
2260            2265                2270                    2275
```

| | | | | | | | | | | | | | | | | |
|---|---|---|---|---|---|---|---|---|---|---|---|---|---|---|---|---|
| GCA | CTA | ACC | AAA | TTA | CAG | CCA | CTT | CTT | AAT | AAG | GAC | TCG | CCT | CTG | CAC | 7159 |
| Ala | Leu | Thr | Lys | Leu | Gln | Pro | Leu | Leu | Asn | Lys | Asp | Ser | Pro | Leu | His | |
| | | | 2280 | | | | | 2285 | | | | | | 2290 | | |
| AAA | GCC | CTC | TTT | TGG | GTA | GCT | GTG | GCT | GTG | CTG | CAG | CTT | GAT | GAG | GTC | 7207 |
| Lys | Ala | Leu | Phe | Trp | Val | Ala | Val | Ala | Val | Leu | Gln | Leu | Asp | Glu | Val | |
| | | | 2295 | | | | 2300 | | | | | 2305 | | | | |
| AAC | TTG | TAT | TCA | GCA | GGT | ACC | GCA | CTT | CTT | GAA | CAA | AAC | CTG | CAT | ACT | 7255 |
| Asn | Leu | Tyr | Ser | Ala | Gly | Thr | Ala | Leu | Leu | Glu | Gln | Asn | Leu | His | Thr | |
| | | 2310 | | | | | 2315 | | | | | 2320 | | | | |
| TTA | GAT | AGT | CTC | CGT | ATA | TTC | AAT | GAC | AAG | AGT | CCA | GAG | GAA | GTA | TTT | 7303 |
| Leu | Asp | Ser | Leu | Arg | Ile | Phe | Asn | Asp | Lys | Ser | Pro | Glu | Glu | Val | Phe | |
| | | 2325 | | | | | 2330 | | | | | 2335 | | | | |
| ATG | GCA | ATC | CGG | AAT | CCT | CTG | GAG | TGG | CAC | TGC | AAG | CAA | ATG | GAT | CAT | 7351 |
| Met | Ala | Ile | Arg | Asn | Pro | Leu | Glu | Trp | His | Cys | Lys | Gln | Met | Asp | His | |
| 2340 | | | | | 2345 | | | | | 2350 | | | | | 2355 | |
| TTT | GTT | GGA | CTC | AAT | TTC | AAC | TCT | AAC | TTT | AAC | TTT | GCA | TTG | GTT | GGA | 7399 |
| Phe | Val | Gly | Leu | Asn | Phe | Asn | Ser | Asn | Phe | Asn | Phe | Ala | Leu | Val | Gly | |
| | | | | 2360 | | | | | 2365 | | | | | 2370 | | |
| CAC | CTT | TTA | AAA | GGG | TAC | AGG | CAT | CCT | TCA | CCT | GCT | ATT | GTT | GCA | AGA | 7447 |
| His | Leu | Leu | Lys | Gly | Tyr | Arg | His | Pro | Ser | Pro | Ala | Ile | Val | Ala | Arg | |
| | | | 2375 | | | | | 2380 | | | | | 2385 | | | |
| ACA | GTC | AGA | ATT | TTA | CAT | ACA | CTA | CTA | ACT | CTG | GTT | AAC | AAA | CAC | AGA | 7495 |
| Thr | Val | Arg | Ile | Leu | His | Thr | Leu | Leu | Thr | Leu | Val | Asn | Lys | His | Arg | |
| | | 2390 | | | | | 2395 | | | | | 2400 | | | | |
| AAT | TGT | GAC | AAA | TTT | GAA | GTG | AAT | ACA | CAG | AGC | GTG | GCC | TAC | TTA | GCA | 7543 |
| Asn | Cys | Asp | Lys | Phe | Glu | Val | Asn | Thr | Gln | Ser | Val | Ala | Tyr | Leu | Ala | |
| | 2405 | | | | | 2410 | | | | | 2415 | | | | | |
| GCT | TTA | CTT | ACA | GTG | TCT | GAA | GAA | GTT | CGA | AGT | CGC | TGC | AGC | CTA | AAA | 7591 |
| Ala | Leu | Leu | Thr | Val | Ser | Glu | Glu | Val | Arg | Ser | Arg | Cys | Ser | Leu | Lys | |
| 2420 | | | | | 2425 | | | | | 2430 | | | | | 2435 | |
| CAT | AGA | AAG | TCA | CTT | CTT | CTT | ACT | GAT | ATT | TCA | ATG | GAA | AAT | GTT | CCT | 7639 |
| His | Arg | Lys | Ser | Leu | Leu | Leu | Thr | Asp | Ile | Ser | Met | Glu | Asn | Val | Pro | |
| | | | | 2440 | | | | | 2445 | | | | | 2450 | | |
| ATG | GAT | ACA | TAT | CCC | ATT | CAT | CAT | GGT | GAC | CCT | TCC | TAT | AGG | ACA | CTA | 7687 |
| Met | Asp | Thr | Tyr | Pro | Ile | His | His | Gly | Asp | Pro | Ser | Tyr | Arg | Thr | Leu | |
| | | | 2455 | | | | | 2460 | | | | | 2465 | | | |
| AAG | GAG | ACT | CAG | CCA | TGG | TCC | TCT | CCC | AAA | GGT | TCT | GAA | GGA | TAC | CTT | 7735 |
| Lys | Glu | Thr | Gln | Pro | Trp | Ser | Ser | Pro | Lys | Gly | Ser | Glu | Gly | Tyr | Leu | |
| | | 2470 | | | | | 2475 | | | | | 2480 | | | | |
| GCA | GCC | ACC | TAT | CCA | ACT | GTC | GGC | CAG | ACC | AGT | CCC | CGA | GCC | AGG | AAA | 7783 |
| Ala | Ala | Thr | Tyr | Pro | Thr | Val | Gly | Gln | Thr | Ser | Pro | Arg | Ala | Arg | Lys | |
| | | 2485 | | | | | 2490 | | | | | 2495 | | | | |
| TCC | ATG | AGC | CTG | GAC | ATG | GGG | CAA | CCT | TCT | CAG | GCC | AAC | ACT | AAG | AAG | 7831 |
| Ser | Met | Ser | Leu | Asp | Met | Gly | Gln | Pro | Ser | Gln | Ala | Asn | Thr | Lys | Lys | |
| 2500 | | | | | 2505 | | | | | 2510 | | | | | 2515 | |
| TTG | CTT | GGA | ACA | AGG | AAA | AGT | TTT | GAT | CAC | TTG | ATA | TCA | GAC | ACA | AAG | 7879 |
| Leu | Leu | Gly | Thr | Arg | Lys | Ser | Phe | Asp | His | Leu | Ile | Ser | Asp | Thr | Lys | |
| | | | | 2520 | | | | | 2525 | | | | | 2530 | | |
| GCT | CCT | AAA | AGG | CAA | GAA | ATG | GAA | TCA | GGG | ATC | ACA | ACA | CCC | CCC | AAA | 7927 |
| Ala | Pro | Lys | Arg | Gln | Glu | Met | Glu | Ser | Gly | Ile | Thr | Thr | Pro | Pro | Lys | |
| | | | 2535 | | | | | 2540 | | | | | 2545 | | | |
| ATG | AGG | AGA | GTA | GCA | GAA | ACT | GAT | TAT | GAA | ATG | GAA | ACT | CAG | AGG | ATT | 7975 |
| Met | Arg | Arg | Val | Ala | Glu | Thr | Asp | Tyr | Glu | Met | Glu | Thr | Gln | Arg | Ile | |
| | | | 2550 | | | | | 2555 | | | | | 2560 | | | |
| TCC | TCA | TCA | CAA | CAG | CAC | CCA | CAT | TTA | CGT | AAA | GTT | TCA | GTG | TCT | GAA | 8023 |
| Ser | Ser | Ser | Gln | Gln | His | Pro | His | Leu | Arg | Lys | Val | Ser | Val | Ser | Glu | |
| | | 2565 | | | | | 2570 | | | | | 2575 | | | | |
| TCA | AAT | GTT | CTC | TTG | GAT | GAA | GAA | GTA | CTT | ACT | GAT | CCG | AAG | ATC | CAG | 8071 |
| Ser | Asn | Val | Leu | Leu | Asp | Glu | Glu | Val | Leu | Thr | Asp | Pro | Lys | Ile | Gln | |
| | 2580 | | | | | 2585 | | | | | 2590 | | | | | 2595 |

| | | | | | | | | | | | | | | | | |
|---|---|---|---|---|---|---|---|---|---|---|---|---|---|---|---|---|
| GCG | CTG | CTT | CTT | ACT | GTT | CTA | GCT | ACA | CTG | GTA | AAA | TAT | ACC | ACA | GAT | 8119 |
| Ala | Leu | Leu | Leu | Thr | Val | Leu | Ala | Thr | Leu | Val | Lys | Tyr | Thr | Thr | Asp | |
| | | | | 2600 | | | | | 2605 | | | | | 2610 | | |
| GAG | TTT | GAT | CAA | CGA | ATT | CTT | TAT | GAA | TAC | TTA | GCA | GAG | GCC | AGT | GTT | 8167 |
| Glu | Phe | Asp | Gln | Arg | Ile | Leu | Tyr | Glu | Tyr | Leu | Ala | Glu | Ala | Ser | Val | |
| | | | | 2615 | | | | | 2620 | | | | | 2625 | | |
| GTG | TTT | CCC | AAA | GTC | TTT | CCT | GTT | GTG | CAT | AAT | TTG | TTG | GAC | TCT | AAG | 8215 |
| Val | Phe | Pro | Lys | Val | Phe | Pro | Val | Val | His | Asn | Leu | Leu | Asp | Ser | Lys | |
| | | | | 2630 | | | | | 2635 | | | | | 2640 | | |
| ATC | AAC | ACC | CTG | TTA | TCA | TTG | TGC | CAA | GAT | CCA | AAT | TTG | TTA | AAT | CCA | 8263 |
| Ile | Asn | Thr | Leu | Leu | Ser | Leu | Cys | Gln | Asp | Pro | Asn | Leu | Leu | Asn | Pro | |
| 2645 | | | | | 2650 | | | | | 2655 | | | | | | |
| ATC | CAT | GGA | ATT | GTG | CAG | AGT | GTG | GTG | TAC | CAT | GAA | GAA | TCC | CCA | CCA | 8311 |
| Ile | His | Gly | Ile | Val | Gln | Ser | Val | Val | Tyr | His | Glu | Glu | Ser | Pro | Pro | |
| 2660 | | | | | 2665 | | | | | 2670 | | | | | 2675 | |
| CAA | TAC | CAA | ACA | TCT | TAC | CTG | CAA | AGT | TTT | GGT | TTT | AAT | GGC | TTG | TGG | 8359 |
| Gln | Tyr | Gln | Thr | Ser | Tyr | Leu | Gln | Ser | Phe | Gly | Phe | Asn | Gly | Leu | Trp | |
| | | | | 2680 | | | | | 2685 | | | | | 2690 | | |
| CGG | TTT | GCA | GGA | CCG | TTT | TCA | AAG | CAA | ACA | CAA | ATT | CCA | GAC | TAT | GCT | 8407 |
| Arg | Phe | Ala | Gly | Pro | Phe | Ser | Lys | Gln | Thr | Gln | Ile | Pro | Asp | Tyr | Ala | |
| | | | | 2695 | | | | | 2700 | | | | | 2705 | | |
| GAG | CTT | ATT | GTT | AAG | TTT | CTT | GAT | GCC | TTG | ATT | GAC | ACG | TAC | CTG | CCT | 8455 |
| Glu | Leu | Ile | Val | Lys | Phe | Leu | Asp | Ala | Leu | Ile | Asp | Thr | Tyr | Leu | Pro | |
| | | | | 2710 | | | | | 2715 | | | | | 2720 | | |
| GGA | ATT | GAT | GAA | GAA | ACC | AGT | GAA | GAA | TCC | CTC | CTG | ACT | CCC | ACA | TCT | 8503 |
| Gly | Ile | Asp | Glu | Glu | Thr | Ser | Glu | Glu | Ser | Leu | Leu | Thr | Pro | Thr | Ser | |
| | | | | 2725 | | | | | 2730 | | | | | 2735 | | |
| CCT | TAC | CCT | CCT | GCA | CTG | CAG | AGC | CAG | CTT | AGT | ATC | ACT | GCC | AAC | CTT | 8551 |
| Pro | Tyr | Pro | Pro | Ala | Leu | Gln | Ser | Gln | Leu | Ser | Ile | Thr | Ala | Asn | Leu | |
| 2740 | | | | | 2745 | | | | | 2750 | | | | | 2755 | |
| AAC | CTT | TCT | AAT | TCC | ATG | ACC | TCA | CTT | GCA | ACT | TCC | CAG | CAT | TCC | CCA | 8599 |
| Asn | Leu | Ser | Asn | Ser | Met | Thr | Ser | Leu | Ala | Thr | Ser | Gln | His | Ser | Pro | |
| | | | | 2760 | | | | | 2765 | | | | | 2770 | | |
| GGA | ATC | GAC | AAG | GAG | AAC | GTT | GAA | CTC | TCC | CCT | ACC | ACT | GGC | CAC | TGT | 8647 |
| Gly | Ile | Asp | Lys | Glu | Asn | Val | Glu | Leu | Ser | Pro | Thr | Thr | Gly | His | Cys | |
| | | | | 2775 | | | | | 2780 | | | | | 2785 | | |
| AAC | AGT | GGA | CGA | ACT | CGC | CAC | GGA | TCC | GCA | AGC | CAA | GTG | CAG | AAG | CAA | 8695 |
| Asn | Ser | Gly | Arg | Thr | Arg | His | Gly | Ser | Ala | Ser | Gln | Val | Gln | Lys | Gln | |
| | | | | 2790 | | | | | 2795 | | | | | 2800 | | |
| AGA | AGC | GCT | GGC | AGT | TTC | AAA | CGT | AAT | AGC | ATT | AAG | AAG | ATC | GTG | | 8740 |
| Arg | Ser | Ala | Gly | Ser | Phe | Lys | Arg | Asn | Ser | Ile | Lys | Lys | Ile | Val | | |
| | | | 2805 | | | | | 2810 | | | | | 2815 | | | |

```
TGAAGCTTGC TTGCTTTCTT TTTTAAAATC AACTTAACAT GGGCTCTTCA CTAGTGACCC      8800
CTTCCCTGTC CTTGCCCTTT CCCCCCATGT TGTAATGCTG CACTTCCTGT TTTATAATGA      8860
ACCCATCCGG TTTGCCATGT TGCCAGATGA TCAACTCTTC GAAGCCTTGC CTAAATTTAA      8920
TGCTGCCTTT TCTTTAACTT TTTTTCTTCT ACTTTTGGCG TGTATCTGGT ATATGTAAGT      8980
GTTCAGAACA ACTGCAAAGA AAGTGGGAGG TCAGGAAACT TTTAACTGAG AAATCTCAAT      9040
TGTAAGAGAG GATGAATTCT TGAATACTGC TACTACTGGC CAGTGATGAA AGCCATTTGC      9100
ACAGAGCTCT GCCTTCTGTG GTTTTCCCTT CTTCATCCTA CAGAGTAAAG TGTTAGTCAG      9160
ATTAAACAGA AAAATGAGAA TACAGGGAGT TACCGATGTT GGTGGTGGTT GTTCTTTACT      9220
TTTGTAATCT GTGCCATTGG AAAGTGAGAG GCAGTGAGCA CCTATTGCTG GAGGTGTGCA      9280
AACAGCATCT GACCTTACTG ATGAATTGAT AACAATGTGG TATGTGATAT TCAAGGGGAG      9340
GTGGTTCATG AGACCGCTCT GGTCTGGAGG TTGCAGAACT CCAGGATCTG TGGTTAGGCC      9400
CTGGGACAGG GGAGCTGGTG CTCTGAGGTG CCTGGCAGAA GCTTCTGGGA GCTTGGGGCT      9460
```

| | | | | | |
|---|---|---|---|---|---|
| AGAGGAGGAC | AAAGGGTAAT | GCTGTCTGAT | GGAAGGGCCG | GGTTCACACA | GAAGCTTGGA | 9520
| CCACACCAGC | ATGGCTGACT | TGGGCCTCTG | GAGTACAGGA | AGATAAGGTG | GGCCTGGTCC | 9580
| CACCCTTGGA | GGTGTAGCCT | GAGCAGGACT | GTGGCTTAAG | CTCTGGGTGC | AGTGGAGCAC | 9640
| ATGAAGGTAT | GCCACAGGTG | CTTGAGAGAG | GGTCCTGGGC | AGAGCTCATG | GGATTCAAGA | 9700
| AGACTCCTGG | TCCTAAACAG | AAAACAGAGA | GATACAGGGA | GCCAGGGGAC | CAGCGTTTGG | 9760
| ACCTTTCCTC | AGCCTCTTAT | GAATCATGAG | AATTTGGGGA | AACTGCTTCA | ACTCTAAGGC | 9820
| TTGATTCCCA | ATCTGTCAAA | TGGGGCAACA | CTCCCTGCCC | TTCTCACAGT | TAACAGGCAC | 9880
| CCTTTCTTAG | GCAGGGGACT | GTGGCAAGTA | CCTTGTGTGC | TGGCACCAGT | GCACAGAGGC | 9940
| AGGAGAGAGG | TGCCAGTACT | GTCCCCATTT | TATGGCTGAA | ACATTGAGCC | TCACACAGGG | 10000
| GAAAAGCATC | TGCCCAGGAC | CATGGGGCTG | TTGGGTGGAA | GAGCTCGTTC | GCCCCAACAC | 10060
| CACCTGGCTC | TGAAGCCTGT | ATGTTTAACT | GTGTACTGCT | GCCTGCCTCA | CAGGGCTCAG | 10120
| ATGAATGTCA | CAATAGAGGA | AAGAGCTCTG | GAAGCTGTGA | GGTGCTGTTT | AAATATGGCG | 10180
| AGATTTTCCC | TATGGGCAAG | ATCTGCCCTC | TCCTGCAAGG | CCTGCCAGCC | CAGCTCTGAT | 10240
| CCTGCAGCAT | CTGCAGAGAG | AAGGCATGGC | GCACCTGGGT | CAGTGGCAGC | TCTTCCTCAC | 10300
| TGCTCTCCGA | GGACCCCTCC | GTGTTCCTCT | CTGGGGGTGC | TGGGGCCAGG | GTCTTGCTTC | 10360
| TGGCAGGTTT | GGAGTTACTG | TCCTTCTGAG | GGACAAGAC | CTGGATAAGC | ACGTGGTCGG | 10420
| GGAGTGGGGC | ATTTGCTGAG | GGGGAAACAG | CCAGTAGGCA | ATGACCCTCA | GGCACTCTGG | 10480
| TTTCCAGGGG | AGGCAGCGTG | GCCCCTTCCT | GCACATGCAC | AGGGATACCT | GCTGGCCTGA | 10540
| CCTGCCCCAC | AGCCACTGGA | AACATGCTTC | CACCCTGCTA | GCTCCTTCCA | GAGCTGACTC | 10600
| CGAACATGAA | AGGGATTTAT | GACTCCGATG | CAGCTAAAAC | CTGAGGGCTG | CAGGGCTGTT | 10660
| GGCCCAATGT | CTCGACAAGA | GGTGACAGCA | GCCTGGGACA | AGGTTG | | 10706

( 2 ) INFORMATION FOR SEQ ID NO:2:

( i ) SEQUENCE CHARACTERISTICS:
        ( A ) LENGTH: 2818 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Ala His Arg Pro Val Glu Trp Val Gln Ala Val Val Ser Arg
 1               5                  10                  15

Phe Asp Glu Gln Leu Pro Ile Lys Thr Gly Gln Gln Asn Thr His Thr
                20                  25                  30

Lys Val Ser Thr Glu His Asn Lys Glu Cys Leu Ile Asn Ile Ser Lys
            35                  40                  45

Tyr Lys Phe Ser Leu Val Ile Ser Gly Leu Thr Thr Ile Leu Lys Asn
    50                  55                  60

Val Asn Asn Met Arg Ile Phe Gly Glu Ala Ala Glu Lys Asn Leu Tyr
65                  70                  75                  80

Leu Ser Gln Leu Ile Ile Leu Asp Thr Leu Glu Lys Cys Leu Ala Gly
                85                  90                  95

Gln Pro Lys Asp Thr Met Arg Leu Asp Glu Thr Met Leu Val Lys Gln
                100                 105                 110

Leu Leu Pro Glu Ile Cys His Phe Leu His Thr Cys Arg Glu Gly Asn
            115                 120                 125

Gln His Ala Ala Glu Leu Arg Asn Ser Ala Ser Gly Val Leu Phe Ser
    130                 135                 140
```

```
Leu  Ser  Cys  Asn  Asn  Phe  Asn  Ala  Val  Phe  Ser  Arg  Ile  Ser  Thr  Arg
145                      150                      155                      160

Leu  Gln  Glu  Leu  Thr  Val  Cys  Ser  Glu  Asp  Asn  Val  Asp  Val  His  Asp
                    165                      170                      175

Ile  Glu  Leu  Leu  Gln  Tyr  Ile  Asn  Val  Asp  Cys  Ala  Lys  Leu  Lys  Arg
                    180                      185                      190

Leu  Leu  Lys  Glu  Thr  Ala  Phe  Lys  Phe  Lys  Ala  Leu  Lys  Lys  Val  Ala
               195                      200                      205

Gln  Leu  Ala  Val  Ile  Asn  Ser  Leu  Glu  Lys  Ala  Phe  Trp  Asn  Trp  Val
210                      215                      220

Glu  Asn  Tyr  Pro  Asp  Glu  Phe  Thr  Lys  Leu  Tyr  Gln  Ile  Pro  Gln  Thr
225                      230                      235                      240

Asp  Met  Ala  Glu  Cys  Ala  Glu  Lys  Leu  Phe  Asp  Leu  Val  Asp  Gly  Phe
                    245                      250                      255

Ala  Glu  Ser  Thr  Lys  Arg  Lys  Ala  Ala  Val  Trp  Pro  Leu  Gln  Ile  Ile
               260                      265                      270

Leu  Leu  Ile  Leu  Cys  Pro  Glu  Ile  Ile  Gln  Asp  Ile  Ser  Lys  Asp  Val
               275                      280                      285

Val  Asp  Glu  Asn  Asn  Met  Asn  Lys  Lys  Leu  Phe  Leu  Asp  Ser  Leu  Arg
     290                      295                      300

Lys  Ala  Leu  Ala  Gly  His  Gly  Gly  Ser  Arg  Gln  Leu  Thr  Glu  Ser  Ala
305                      310                      315                      320

Ala  Ile  Ala  Cys  Val  Lys  Leu  Cys  Lys  Ala  Ser  Thr  Tyr  Ile  Asn  Trp
                    325                      330                      335

Glu  Asp  Asn  Ser  Val  Ile  Phe  Leu  Leu  Val  Gln  Ser  Met  Val  Val  Asp
               340                      345                      350

Leu  Lys  Asn  Leu  Leu  Phe  Asn  Pro  Ser  Lys  Pro  Phe  Ser  Arg  Gly  Ser
          355                      360                      365

Gln  Pro  Ala  Asp  Val  Asp  Leu  Met  Ile  Asp  Cys  Leu  Val  Ser  Cys  Phe
370                      375                      380

Arg  Ile  Ser  Pro  His  Asn  Asn  Gln  His  Phe  Lys  Ile  Cys  Leu  Ala  Gln
385                      390                      395                      400

Asn  Ser  Pro  Ser  Thr  Phe  His  Tyr  Val  Leu  Val  Asn  Ser  Leu  His  Arg
                    405                      410                      415

Ile  Ile  Thr  Asn  Ser  Ala  Leu  Asp  Trp  Trp  Pro  Lys  Ile  Asp  Ala  Val
               420                      425                      430

Tyr  Cys  His  Ser  Val  Glu  Leu  Arg  Asn  Met  Phe  Gly  Glu  Thr  Leu  His
          435                      440                      445

Lys  Ala  Val  Gln  Gly  Cys  Gly  Ala  His  Pro  Ala  Ile  Arg  Met  Ala  Pro
     450                      455                      460

Ser  Leu  Thr  Phe  Lys  Glu  Lys  Val  Thr  Ser  Leu  Lys  Phe  Lys  Glu  Lys
465                      470                      475                      480

Pro  Thr  Asp  Leu  Glu  Thr  Arg  Ser  Tyr  Lys  Tyr  Leu  Leu  Leu  Ser  Ile
                    485                      490                      495

Val  Lys  Leu  Ile  His  Ala  Asp  Pro  Lys  Leu  Leu  Leu  Cys  Asn  Pro  Arg
               500                      505                      510

Lys  Gln  Gly  Pro  Glu  Thr  Gln  Gly  Ser  Thr  Ala  Glu  Leu  Ile  Thr  Gly
     515                      520                      525

Leu  Val  Gln  Leu  Val  Pro  Gln  Ser  His  Met  Pro  Glu  Ile  Ala  Gln  Glu
     530                      535                      540

Ala  Met  Glu  Ala  Leu  Leu  Val  Leu  His  Gln  Leu  Asp  Ser  Ile  Asp  Leu
545                      550                      555                      560

Trp  Asn  Pro  Asp  Ala  Pro  Val  Glu  Thr  Phe  Trp  Glu  Ile  Ser  Ser  Gln
```

```
                565                           570                           575
Met  Leu  Phe  Tyr  Ile  Cys  Lys  Lys  Leu  Thr  Ser  His  Gln  Met  Leu  Ser
               580                      585                      590

Ser  Thr  Glu  Ile  Leu  Lys  Trp  Leu  Arg  Glu  Ile  Leu  Ile  Cys  Arg  Asn
          595                      600                      605

Lys  Phe  Leu  Leu  Lys  Asn  Lys  Gln  Ala  Asp  Arg  Ser  Ser  Cys  His  Phe
     610                 615                      620

Leu  Leu  Phe  Tyr  Gly  Val  Gly  Cys  Asp  Ile  Pro  Ser  Ser  Gly  Asn  Thr
625                      630                      635                           640

Ser  Gln  Met  Ser  Met  Asp  His  Glu  Glu  Leu  Leu  Arg  Thr  Pro  Gly  Ala
                    645                      650                      655

Ser  Leu  Arg  Lys  Gly  Lys  Gly  Asn  Ser  Ser  Met  Asp  Ser  Ala  Ala  Gly
               660                      665                      670

Cys  Ser  Gly  Thr  Pro  Pro  Ile  Cys  Arg  Gln  Ala  Gln  Thr  Lys  Leu  Glu
          675                      680                      685

Val  Ala  Leu  Tyr  Met  Phe  Leu  Trp  Asn  Pro  Asp  Thr  Glu  Ala  Val  Leu
     690                      695                      700

Val  Ala  Met  Ser  Cys  Phe  Arg  His  Leu  Cys  Glu  Glu  Ala  Asp  Ile  Arg
705                      710                      715                           720

Cys  Gly  Val  Asp  Glu  Val  Ser  Val  His  Asn  Leu  Leu  Pro  Asn  Tyr  Asn
               725                      730                      735

Thr  Phe  Met  Glu  Phe  Ala  Ser  Val  Ser  Asn  Met  Met  Ser  Thr  Gly  Arg
               740                      745                      750

Ala  Ala  Leu  Gln  Lys  Arg  Val  Met  Ala  Leu  Leu  Arg  Arg  Ile  Glu  His
          755                      760                      765

Pro  Thr  Ala  Gly  Asn  Thr  Glu  Ala  Trp  Glu  Asp  Thr  His  Ala  Lys  Trp
     770                      775                      780

Glu  Gln  Ala  Thr  Lys  Leu  Ile  Leu  Asn  Tyr  Pro  Lys  Ala  Lys  Met  Glu
785                      790                      795                           800

Asp  Gly  Gln  Ala  Ala  Glu  Ser  Leu  His  Lys  Thr  Ile  Val  Lys  Arg  Arg
               805                      810                      815

Met  Ser  His  Val  Ser  Gly  Gly  Gly  Ser  Ile  Asp  Leu  Ser  Asp  Thr  Asp
               820                      825                      830

Ser  Leu  Gln  Glu  Trp  Ile  Asn  Met  Thr  Gly  Phe  Leu  Cys  Ala  Leu  Gly
          835                      840                      845

Gly  Val  Cys  Leu  Gln  Gln  Arg  Ser  Asn  Ser  Gly  Leu  Ala  Thr  Tyr  Ser
850                      855                      860

Pro  Pro  Met  Gly  Pro  Val  Ser  Glu  Arg  Lys  Gly  Ser  Met  Ile  Ser  Val
865                      870                      875                           880

Met  Ser  Ser  Glu  Gly  Asn  Ala  Asp  Thr  Pro  Val  Ser  Lys  Phe  Met  Asp
               885                      890                      895

Arg  Leu  Leu  Ser  Leu  Met  Val  Cys  Asn  His  Glu  Lys  Val  Gly  Leu  Gln
               900                      905                      910

Ile  Arg  Thr  Asn  Val  Lys  Asp  Leu  Val  Gly  Leu  Glu  Leu  Ser  Pro  Ala
          915                      920                      925

Leu  Tyr  Pro  Met  Leu  Phe  Asn  Lys  Leu  Lys  Asn  Thr  Ile  Ser  Lys  Phe
     930                      935                      940

Phe  Asp  Ser  Gln  Gly  Gln  Val  Leu  Leu  Thr  Asp  Thr  Asn  Thr  Gln  Phe
945                      950                      955                           960

Val  Glu  Gln  Thr  Ile  Ala  Ile  Met  Lys  Asn  Leu  Leu  Asp  Asn  His  Thr
               965                      970                      975

Glu  Gly  Ser  Ser  Glu  His  Leu  Gly  Gln  Ala  Ser  Ile  Glu  Thr  Met  Met
               980                      985                      990
```

```
Leu  Asn  Leu  Val  Arg  Tyr  Val  Arg  Val  Leu  Gly  Asn  Met  Val  His  Ala
          995                      1000                     1005

Ile  Gln  Ile  Lys  Thr  Lys  Leu  Cys  Gln  Leu  Val  Glu  Val  Met  Met  Ala
     1010                     1015                     1020

Arg  Arg  Asp  Asp  Leu  Ser  Phe  Cys  Gln  Glu  Met  Lys  Phe  Arg  Asn  Lys
1025                     1030                     1035                     1040

Met  Val  Glu  Tyr  Leu  Thr  Asp  Trp  Val  Met  Gly  Thr  Ser  Asn  Gln  Ala
               1045                     1050                     1055

Ala  Asp  Asp  Asp  Val  Lys  Cys  Leu  Thr  Arg  Asp  Leu  Asp  Gln  Ala  Ser
               1060                     1065                     1070

Met  Glu  Ala  Val  Val  Ser  Leu  Leu  Ala  Gly  Leu  Pro  Leu  Gln  Pro  Glu
          1075                     1080                     1085

Glu  Gly  Asp  Gly  Val  Glu  Leu  Met  Glu  Ala  Lys  Ser  Gln  Leu  Phe  Leu
          1090                     1095                     1100

Lys  Tyr  Phe  Thr  Leu  Phe  Met  Asn  Leu  Leu  Asn  Asp  Cys  Ser  Glu  Val
1105                     1110                     1115                     1120

Glu  Asp  Glu  Ser  Ala  Gln  Thr  Gly  Gly  Arg  Lys  Arg  Gly  Met  Ser  Arg
                    1125                     1130                     1135

Arg  Leu  Ala  Ser  Leu  Arg  His  Cys  Thr  Val  Leu  Ala  Met  Ser  Asn  Leu
               1140                     1145                     1150

Leu  Asn  Ala  Asn  Val  Asp  Ser  Gly  Leu  Met  His  Ser  Ile  Gly  Leu  Gly
               1155                     1160                     1165

Tyr  His  Lys  Asp  Leu  Gln  Thr  Arg  Ala  Thr  Phe  Met  Glu  Val  Leu  Thr
     1170                     1175                     1180

Lys  Ile  Leu  Gln  Gln  Gly  Thr  Glu  Phe  Asp  Thr  Leu  Ala  Glu  Thr  Val
1185                     1190                     1195                     1200

Leu  Ala  Asp  Arg  Phe  Glu  Arg  Leu  Val  Glu  Leu  Val  Thr  Met  Met  Gly
                    1205                     1210                     1215

Asp  Gln  Gly  Glu  Leu  Pro  Ile  Ala  Met  Ala  Leu  Ala  Asn  Val  Val  Pro
                    1220                     1225                     1230

Cys  Ser  Gln  Trp  Asp  Glu  Leu  Ala  Arg  Val  Leu  Val  Thr  Leu  Phe  Asp
               1235                     1240                     1245

Ser  Arg  His  Leu  Leu  Tyr  Gln  Leu  Leu  Trp  Asn  Met  Phe  Ser  Lys  Glu
     1250                     1255                     1260

Val  Glu  Leu  Ala  Asp  Ser  Met  Gln  Thr  Leu  Phe  Arg  Gly  Asn  Ser  Leu
1265                     1270                     1275                     1280

Ala  Ser  Lys  Ile  Met  Thr  Phe  Cys  Phe  Lys  Val  Tyr  Gly  Ala  Thr  Tyr
                    1285                     1290                     1295

Leu  Gln  Lys  Leu  Leu  Asp  Pro  Leu  Leu  Arg  Ile  Val  Ile  Thr  Ser  Ser
               1300                     1305                     1310

Asp  Trp  Gln  His  Val  Ser  Phe  Glu  Val  Asp  Pro  Thr  Arg  Leu  Glu  Pro
          1315                     1320                     1325

Ser  Glu  Ser  Leu  Glu  Glu  Asn  Gln  Arg  Asn  Leu  Leu  Gln  Met  Thr  Glu
          1330                     1335                     1340

Lys  Phe  Phe  His  Ala  Ile  Ile  Ser  Ser  Ser  Ser  Glu  Phe  Pro  Pro  Gln
1345                     1350                     1355                     1360

Leu  Arg  Ser  Val  Cys  His  Cys  Leu  Tyr  Gln  Val  Val  Ser  Gln  Arg  Phe
                    1365                     1370                     1375

Pro  Gln  Asn  Ser  Ile  Gly  Ala  Val  Gly  Ser  Ala  Met  Phe  Leu  Arg  Phe
               1380                     1385                     1390

Ile  Asn  Pro  Ala  Ile  Val  Ser  Pro  Tyr  Glu  Ala  Gly  Ile  Leu  Asp  Lys
               1395                     1400                     1405

Lys  Pro  Pro  Pro  Arg  Ile  Glu  Arg  Gly  Leu  Lys  Leu  Met  Ser  Lys  Ile
          1410                     1415                     1420
```

```
Leu Gln Ser Ile Ala Asn His Val Leu Phe Thr Lys Glu Glu His Met
1425                1430                1435                    1440

Arg Pro Phe Asn Asp Phe Val Lys Ser Asn Phe Asp Ala Ala Arg Arg
                1445                1450                1455

Phe Phe Leu Asp Ile Ala Ser Asp Cys Pro Thr Ser Asp Ala Val Asn
            1460                1465                1470

His Ser Leu Ser Phe Ile Ser Asp Gly Asn Val Leu Ala Leu His Arg
            1475                1480                1485

Leu Leu Trp Asn Asn Gln Glu Lys Ile Gly Gln Tyr Leu Ser Ser Asn
        1490                1495                1500

Arg Asp His Lys Ala Val Gly Arg Arg Pro Phe Asp Lys Met Ala Thr
1505                1510                1515                    1520

Leu Leu Ala Tyr Leu Gly Pro Pro Glu His Lys Pro Val Ala Asp Thr
            1525                1530                1535

His Trp Ser Ser Leu Asn Leu Thr Ser Ser Lys Phe Glu Glu Phe Met
        1540                1545                1550

Thr Arg His Gln Val His Glu Lys Glu Glu Phe Lys Ala Leu Lys Thr
        1555                1560                1565

Leu Ser Ile Phe Tyr Gln Ala Gly Thr Ser Lys Ala Gly Asn Pro Ile
        1570                1575                1580

Phe Tyr Tyr Val Ala Arg Arg Phe Lys Thr Gly Gln Ile Asn Gly Asp
1585                1590                1595                    1600

Leu Leu Ile Tyr His Val Leu Leu Thr Leu Lys Pro Tyr Tyr Ala Lys
            1605                1610                1615

Pro Tyr Glu Ile Val Val Asp Leu Thr His Thr Gly Pro Ser Asn Arg
            1620                1625                1630

Phe Lys Thr Asp Phe Leu Ser Lys Trp Phe Val Phe Pro Gly Phe
            1635                1640                1645

Ala Tyr Asp Asn Val Ser Ala Val Tyr Ile Tyr Asn Cys Asn Ser Trp
            1650                1655                1660

Val Arg Glu Tyr Thr Lys Tyr His Glu Arg Leu Leu Thr Gly Leu Lys
1665                1670                1675                    1680

Gly Ser Lys Arg Leu Val Phe Ile Asp Cys Pro Gly Lys Leu Ala Glu
            1685                1690                1695

His Ile Glu His Glu Gln Gln Lys Leu Pro Ala Ala Thr Leu Ala Leu
        1700                1705                1710

Glu Glu Asp Leu Lys Val Phe His Asn Ala Leu Lys Leu Ala His Lys
        1715                1720                1725

Asp Thr Lys Val Ser Ile Lys Val Gly Ser Thr Ala Val Gln Val Thr
        1730                1735                1740

Ser Ala Glu Arg Thr Lys Val Leu Gly Gln Ser Val Phe Leu Asn Asp
1745                1750                1755                    1760

Ile Tyr Tyr Ala Ser Glu Ile Glu Glu Ile Cys Leu Val Asp Glu Asn
            1765                1770                1775

Gln Phe Thr Leu Thr Ile Ala Asn Gln Gly Thr Pro Leu Thr Phe Met
            1780                1785                1790

His Gln Glu Cys Glu Ala Ile Val Gln Ser Ile Ile His Ile Arg Thr
        1795                1800                1805

Arg Trp Glu Leu Ser Gln Pro Asp Ser Ile Pro Gln His Thr Lys Ile
        1810                1815                1820

Arg Pro Lys Asp Val Pro Gly Thr Leu Leu Asn Ile Ala Leu Leu Asn
1825                1830                1835                    1840

Leu Gly Ser Ser Asp Pro Ser Leu Arg Ser Ala Ala Tyr Asn Leu Leu
```

```
                    1845                    1850                    1855
Cys  Ala  Leu  Thr  Cys  Thr  Phe  Asn  Leu  Lys  Ile  Glu  Gly  Gln  Leu  Leu
               1860                    1865                    1870

Glu  Thr  Ser  Gly  Leu  Cys  Ile  Pro  Ala  Asn  Asn  Thr  Leu  Phe  Ile  Val
               1875                    1880                    1885

Ser  Ile  Ser  Lys  Thr  Leu  Ala  Ala  Asn  Glu  Pro  His  Leu  Thr  Leu  Glu
               1890                    1895                    1900

Phe  Leu  Glu  Glu  Cys  Ile  Ser  Gly  Phe  Ser  Lys  Ser  Ser  Ile  Glu  Leu
1905                    1910                    1915                    1920

Lys  His  Leu  Cys  Leu  Glu  Tyr  Met  Thr  Pro  Trp  Leu  Ser  Asn  Leu  Val
               1925                    1930                    1935

Arg  Phe  Cys  Lys  His  Asn  Asp  Asp  Ala  Lys  Arg  Gln  Arg  Val  Thr  Ala
               1940                    1945                    1950

Ile  Leu  Asp  Lys  Leu  Ile  Thr  Met  Thr  Ile  Asn  Glu  Lys  Gln  Met  Tyr
               1955                    1960                    1965

Pro  Ser  Ile  Gln  Ala  Lys  Ile  Trp  Gly  Ser  Leu  Gly  Gln  Ile  Thr  Asp
               1970                    1975                    1980

Leu  Leu  Asp  Val  Val  Leu  Asp  Ser  Phe  Ile  Lys  Thr  Ser  Ala  Thr  Gly
1985                    1990                    1995                    2000

Gly  Leu  Gly  Ser  Ile  Lys  Ala  Glu  Val  Met  Ala  Asp  Thr  Ala  Val  Ala
               2005                    2010                    2015

Leu  Ala  Ser  Gly  Asn  Val  Lys  Leu  Val  Ser  Ser  Lys  Val  Ile  Gly  Arg
               2020                    2025                    2030

Met  Cys  Lys  Ile  Ile  Asp  Lys  Thr  Cys  Leu  Ser  Pro  Thr  Pro  Thr  Leu
               2035                    2040                    2045

Glu  Gln  His  Leu  Met  Trp  Asp  Asp  Ile  Ala  Ile  Leu  Ala  Arg  Tyr  Met
               2050                    2055                    2060

Leu  Met  Leu  Ser  Phe  Asn  Asn  Ser  Leu  Asp  Val  Ala  Ala  His  Leu  Pro
2065                    2070                    2075                    2080

Tyr  Leu  Phe  His  Val  Val  Thr  Phe  Leu  Val  Ala  Thr  Gly  Pro  Leu  Ser
               2085                    2090                    2095

Leu  Arg  Ala  Ser  Thr  His  Gly  Leu  Val  Ile  Asn  Ile  Ile  His  Ser  Leu
               2100                    2105                    2110

Cys  Thr  Cys  Ser  Gln  Leu  His  Phe  Ser  Glu  Glu  Thr  Lys  Gln  Val  Leu
               2115                    2120                    2125

Arg  Leu  Ser  Leu  Thr  Glu  Phe  Ser  Leu  Pro  Lys  Phe  Tyr  Leu  Leu  Phe
               2130                    2135                    2140

Gly  Ile  Ser  Lys  Val  Lys  Ser  Ala  Ala  Val  Ile  Ala  Phe  Arg  Ser  Ser
2145                    2150                    2155                    2160

Tyr  Arg  Asp  Arg  Ser  Phe  Ser  Pro  Gly  Ser  Tyr  Glu  Arg  Glu  Thr  Phe
               2165                    2170                    2175

Ala  Leu  Thr  Ser  Leu  Glu  Thr  Val  Thr  Glu  Ala  Leu  Leu  Glu  Ile  Met
               2180                    2185                    2190

Glu  Ala  Cys  Met  Arg  Asp  Ile  Pro  Thr  Cys  Lys  Trp  Leu  Asp  Gln  Trp
               2195                    2200                    2205

Thr  Glu  Leu  Ala  Gln  Arg  Phe  Ala  Phe  Gln  Tyr  Asn  Pro  Ser  Leu  Gln
               2210                    2215                    2220

Pro  Arg  Ala  Leu  Val  Val  Phe  Gly  Cys  Ile  Ser  Lys  Arg  Val  Ser  His
2225                    2230                    2235                    2240

Gly  Gln  Ile  Lys  Gln  Ile  Ile  Arg  Ile  Leu  Ser  Lys  Ala  Leu  Glu  Ser
               2245                    2250                    2255

Cys  Leu  Lys  Gly  Pro  Asp  Thr  Tyr  Asn  Ser  Gln  Val  Leu  Ile  Glu  Ala
               2260                    2265                    2270
```

```
Thr Val Ile Ala Leu Thr Lys Leu Gln Pro Leu Leu Asn Lys Asp Ser
         2275                2280                2285

Pro Leu His Lys Ala Leu Phe Trp Val Ala Val Ala Val Leu Gln Leu
    2290                2295                2300

Asp Glu Val Asn Leu Tyr Ser Ala Gly Thr Ala Leu Leu Glu Gln Asn
2305                2310                2315                2320

Leu His Thr Leu Asp Ser Leu Arg Ile Phe Asn Asp Lys Ser Pro Glu
                2325                2330                2335

Glu Val Phe Met Ala Ile Arg Asn Pro Leu Glu Trp His Cys Lys Gln
            2340                2345                2350

Met Asp His Phe Val Gly Leu Asn Phe Asn Ser Asn Phe Asn Phe Ala
        2355                2360                2365

Leu Val Gly His Leu Leu Lys Gly Tyr Arg His Pro Ser Pro Ala Ile
    2370                2375                2380

Val Ala Arg Thr Val Arg Ile Leu His Thr Leu Leu Thr Leu Val Asn
2385                2390                2395                2400

Lys His Arg Asn Cys Asp Lys Phe Glu Val Asn Thr Gln Ser Val Ala
                2405                2410                2415

Tyr Leu Ala Ala Leu Leu Thr Val Ser Glu Glu Val Arg Ser Arg Cys
            2420                2425                2430

Ser Leu Lys His Arg Lys Ser Leu Leu Leu Thr Asp Ile Ser Met Glu
        2435                2440                2445

Asn Val Pro Met Asp Thr Tyr Pro Ile His His Gly Asp Pro Ser Tyr
    2450                2455                2460

Arg Thr Leu Lys Glu Thr Gln Pro Trp Ser Ser Pro Lys Gly Ser Glu
2465                2470                2475                2480

Gly Tyr Leu Ala Ala Thr Tyr Pro Thr Val Gly Gln Thr Ser Pro Arg
                2485                2490                2495

Ala Arg Lys Ser Met Ser Leu Asp Met Gly Gln Pro Ser Gln Ala Asn
            2500                2505                2510

Thr Lys Lys Leu Leu Gly Thr Arg Lys Ser Phe Asp His Leu Ile Ser
        2515                2520                2525

Asp Thr Lys Ala Pro Lys Arg Gln Glu Met Glu Ser Gly Ile Thr Thr
    2530                2535                2540

Pro Pro Lys Met Arg Arg Val Ala Glu Thr Asp Tyr Glu Met Glu Thr
2545                2550                2555                2560

Gln Arg Ile Ser Ser Ser Gln Gln His Pro His Leu Arg Lys Val Ser
                2565                2570                2575

Val Ser Glu Ser Asn Val Leu Leu Asp Glu Glu Val Leu Thr Asp Pro
            2580                2585                2590

Lys Ile Gln Ala Leu Leu Leu Thr Val Leu Ala Thr Leu Val Lys Tyr
        2595                2600                2605

Thr Thr Asp Glu Phe Asp Gln Arg Ile Leu Tyr Glu Tyr Leu Ala Glu
    2610                2615                2620

Ala Ser Val Val Phe Pro Lys Val Phe Pro Val Val His Asn Leu Leu
2625                2630                2635                2640

Asp Ser Lys Ile Asn Thr Leu Leu Ser Leu Cys Gln Asp Pro Asn Leu
                2645                2650                2655

Leu Asn Pro Ile His Gly Ile Val Gln Ser Val Val Tyr His Glu Glu
            2660                2665                2670

Ser Pro Pro Gln Tyr Gln Thr Ser Tyr Leu Gln Ser Phe Gly Phe Asn
        2675                2680                2685

Gly Leu Trp Arg Phe Ala Gly Pro Phe Ser Lys Gln Thr Gln Ile Pro
    2690                2695                2700
```

| Asp | Tyr | Ala | Glu | Leu | Ile | Val | Lys | Phe | Leu | Asp | Ala | Leu | Ile | Asp | Thr |
|---|---|---|---|---|---|---|---|---|---|---|---|---|---|---|---|
| 2705 | | | | | 2710 | | | | 2715 | | | | | | 2720 |
| Tyr | Leu | Pro | Gly | Ile | Asp | Glu | Glu | Thr | Ser | Glu | Glu | Ser | Leu | Leu | Thr |
| | | | | 2725 | | | | | 2730 | | | | | 2735 | |
| Pro | Thr | Ser | Pro | Tyr | Pro | Pro | Ala | Leu | Gln | Ser | Gln | Leu | Ser | Ile | Thr |
| | | | 2740 | | | | | 2745 | | | | | 2750 | | |
| Ala | Asn | Leu | Asn | Leu | Ser | Asn | Ser | Met | Thr | Ser | Leu | Ala | Thr | Ser | Gln |
| | | | 2755 | | | | | 2760 | | | | | 2765 | | |
| His | Ser | Pro | Gly | Ile | Asp | Lys | Glu | Asn | Val | Glu | Leu | Ser | Pro | Thr | Thr |
| | | | 2770 | | | | 2775 | | | | | 2780 | | | |
| Gly | His | Cys | Asn | Ser | Gly | Arg | Thr | Arg | His | Gly | Ser | Ala | Ser | Gln | Val |
| 2785 | | | | | 2790 | | | | | 2795 | | | | | 2800 |
| Gln | Lys | Gln | Arg | Ser | Ala | Gly | Ser | Phe | Lys | Arg | Asn | Ser | Ile | Lys | Lys |
| | | | | 2805 | | | | | 2810 | | | | | 2815 | |
| Ile | Val | | | | | | | | | | | | | | |

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:3:

ATAATTGTTG ATGTGATTTT CATTG        25

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:4:

AATTTTGAAC CAGATGAAGA G        21

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:5:

ATCTAGTATT TTTGAGGCCT CAG      23

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: homo sapiens ( x i ) SEQUENCE DESCRIPTION: SEQ ID NO:6:

CAGATATGCT ATAGTACAGA AGG      23

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:7:

CATATCTGTT TTATCATCAG GAGG      24

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Hoomo sapiens ( x i ) SEQUENCE DESCRIPTION: SEQ ID NO:8:

AAGTAAAATG GAGAAAGGAA CTGG      24

( 2 ) INFORMATION FOR SEQ ID NO:9:

( i ) SEQUENCE CHARACTERISTICS:

( A ) LENGTH: 24 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:9:

CAAAATGAAA CATGGAACTT TAGA                                    24

( 2 ) INFORMATION FOR SEQ ID NO:10:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:10:

TAAGCATTAA GTACAAATAG CACA                                    24

( 2 ) INFORMATION FOR SEQ ID NO:11:

( i ) SEQUENCE CHARACTERISTICS:
                ( A ) LENGTH: 26 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:11:

TTTATGTTTG TGCTCTAACA CCAAGT                                  26

( 2 ) INFORMATION FOR SEQ ID NO:12:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:12:

ATAAATGCTA GAATGATTTC TCATGCT    27

( 2 ) INFORMATION FOR SEQ ID NO:13:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:13:

CAAACCTTAT ACTCAATTCT CAACTC    26

( 2 ) INFORMATION FOR SEQ ID NO:14:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:14:

AAGGGGAATT TAAGATAGCT AGATTATC    28

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:15:

GAAAGGGGCT TGAAGTTAAT GTCG    24

( 2 ) INFORMATION FOR SEQ ID NO:16:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

(iii) HYPOTHETICAL: NO (iv) ANTI-SENSE: NO (vi) ORIGINAL SOURCE:
 (A) ORGANISM: Homo sapiens (xi) SEQUENCE DESCRIPTION: SEQ ID NO:16:

GGAGATGGTG TGTCGACCAT GGAAGCCAAA TCACAG         36

(2) INFORMATION FOR SEQ ID NO:17:

(i) SEQUENCE CHARACTERISTICS:
 (A) LENGTH: 30 base pairs
 (B) TYPE: nucleic acid
 (C) STRANDEDNESS: single
 (D) TOPOLOGY: linear (ii) MOLECULE TYPE: DNA (genomic)

(iii) HYPOTHETICAL: NO (iv) ANTI-SENSE: NO (vi) ORIGINAL SOURCE:
 (A) ORGANISM: Homo spaiens (xi) SEQUENCE DESCRIPTION: SEQ ID NO:17:

ACTCTGAAGT ATCTGTGACA TTAACTTCAA         30

(2) INFORMATION FOR SEQ ID NO:18:

(i) SEQUENCE CHARACTERISTICS:
 (A) LENGTH: 30 base pairs
 (B) TYPE: nucleic acid
 (C) STRANDEDNESS: single
 (D) TOPOLOGY: linear (ii) MOLECULE TYPE: DNA (genomic)

(iii) HYPOTHETICAL: NO (iv) ANTI-SENSE: NO (vi) ORIGINAL SOURCE:
 (A) ORGANISM: Homo sapiens (xi) SEQUENCE DESCRIPTION: SEQ ID NO:18:

TTGAAGTTAA TGTCACAGAT ACTTCAGAGT         30

(2) INFORMATION FOR SEQ ID NO:19:

(i) SEQUENCE CHARACTERISTICS:
 (A) LENGTH: 62 base pairs
 (B) TYPE: nucleic acid
 (C) STRANDEDNESS: single
 (D) TOPOLOGY: linear (ii) MOLECULE TYPE: DNA (genomic)

(iii) HYPOTHETICAL: NO (iv) ANTI-SENSE: NO (vi) ORIGINAL SOURCE:
 (A) ORGANISM: Homo sapiens (xi) SEQUENCE DESCRIPTION: SEQ ID NO:19:

TAGGATTCTC TAGAGCTCAT GTTTCTGGTT CTGGTGGTGG TGTTAACGTT TTCAAAGCCT         60
TG         62

(2) INFORMATION FOR SEQ ID NO:20:

(i) SEQUENCE CHARACTERISTICS:
(A) LENGTH: 3 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
(A) ORGANISM: Homo sapiens (xi) SEQUENCE DESCRIPTION: SEQ ID NO:20:

Phe Leu Arg
1

(2) INFORMATION FOR SEQ ID NO:21:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
(A) ORGANISM: Homo sapiens (xi) SEQUENCE DESCRIPTION: SEQ ID NO:21:

Thr Pro Pro Pro Glu Pro Glu Thr
1               5

SOMATIC MUTATIONS IN NEUROFIBROMATOSIS TYPE 1 GENE IN HUMAN TUMORS

CROSS REFERENCE TO RELATED APPLICATION

This application is a continuation of application Ser. No 08/047,088, filed Apr. 16, 1993, now abandoned, which is a continuation-in-part of application Ser. No. 07/551,531, filed Jul. 12, 1990, now U.S. Pat. No. 5,227,292.

BACKGROUND OF THE INVENTION

The present invention relates to somatic mutations of the neurofibromatosis type 1 (NF1) gene in human tumors. The invention further relates to methods for the detection and treatment of humans having somatic mutations in the NF1 genes in tumors.

The publications and other materials used herein to illuminate the background of the invention, and in particular, cases to provide additional details respecting its practice, are incorporated by reference herein and for convenience are numerically referenced in parentheses in the following text and respectively grouped in the appended bibliography.

The neurofibromatoses are genetic disorders that primarily affect cell growth of neural tissues. These disorders can cause tumors to grow on the nerves at any location and at any time. Some manifestations are progressive, and may result in significant morbidity or mortality. Two distinctive forms are recognized, but variant forms may exist.

The most common type, neurofibromatosis type 1 or NF1 (previously known as von Recklinghausen's neurofibromatosis or peripheral neurofibromatosis), is an autosomal dominant disorder affecting about 1 in 3,500 individuals (1). It has been found that the spontaneous mutation rate is quite high, with 30%–50% of NF1 affected individuals representing new mutations. This leads to a calculated mutation rate of about 1/10,000, which is about 100-fold higher than the usual mutation rate for a single locus. One explanation for such a high mutation rate is that the NF1 gene is a megagene which has been confirmed by its cloning and sequencing.

The clinical features of the disorder are startlingly variable, even within the same family, indicating that other events must play a role in the eventual phenotype of the disease. The diagnostic criteria for NF1 include the presence of two or more of the following: (1) six or more café-au-lait macules more than 15 mm in greatest diameter in postpubertal individuals, or 5 mm in prepubertal individuals; (2) two or more neurofibromas of any type, or one plexiform neurofibroma; (3) freckling in the axillary or inguinal regions; (4) optic glioma; (5) two or more Lisch nodules (iris hamartomas); (6) a distinctive bony lesion such as sphenoid dysplasia or thinning of long-bone cortex, with or without pseudoarthrosis; (7) a first-degree relative with NF1 (1). The penetrance of NF1 is extremely high if individuals are carefully examined, including use of a slit-lamp to detect Lisch nodules. Under those circumstances, it is rare to identify an adult obligate gene carrier who does not meet the criteria listed above (2).

The NF1 gene has been identified (3–6). Analysis of the NF1 gene product, neurofibromin, demonstrated that neurofibromin contains a domain showing approximately 30% similarity to the catalytic domains of yeast IRA1 and IRA2 proteins and the mammalian GTPase are activating protein (GAP) (7,8). The yeast IRA genes encode negative regulators of yeast RAS genes that are homologs of mammalian GAP (9–11).

Guanine nucleotide binding to ras proteins mediates signal transduction that regulates cell growth: binding to GTP activates signaling, while hydrolysis to GDP terminates signaling (12). A GTPase-activating protein (GAP) was the first protein found to catalyze the hydrolysis to GDP and thereby mediate the signal termination event (13). In addition to this role, it has been proposed that GAP may also function in signal propagation as a downstream effector of ras (14,15). More recently, the GAP-related domain (GRD) of neurofibromin, the neurofibromatosis 1 (NF1) gene product, was also found to stimulate the GTPase of ras (8,16,17) and to possess properties consistent with the functioning of neurofibromin as a downstream effector of ras (18).

SUMMARY OF THE INVENTION

The present invention is directed to somatic mutations of the NF1 gene which are found in human tumors. In addition, the present invention is directed to methods of screening humans to determine those having somatic mutations in the NF1 gene in tumors. Finally, the invention is directed to a method of treating a human having a tumor with a somatic mutation in the NF1 gene by restoring natural regulation of ras proteins.

DETAILED DESCRIPTION OF THE INVENTION

Figure 1:
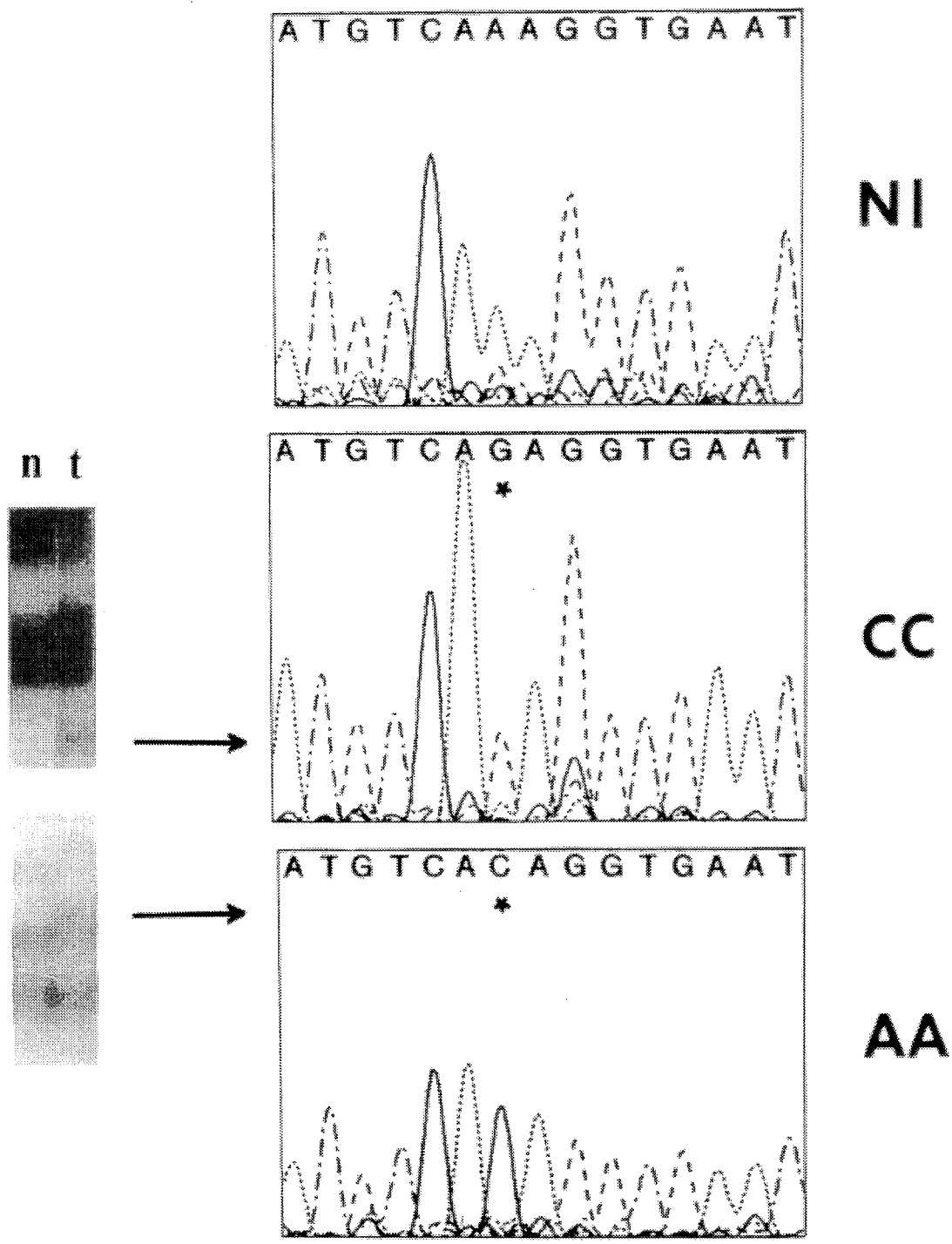
FIG. 1 shows somatic mutations in tumors detected by SSCP and sequenced. On the left, the SSCP patterns obtained from normal (n) tissue and colon cancer tissue (t) from one patient (upper two lanes); and from the normal and anaplastic astrocytoma tissue from another patient (lower two lanes). On the right, the sequences of the normal (Nl) and mutant alleles: colon cancer (CC) and anaplastic astrocytoma (AA). Arrows indicate the specific variant bands that were cut from SSCP gels to obtain the sequences shown.

The present invention is directed to somatic mutations of the NF1 gene which are found in human tumors. In addition, the present invention is directed to methods of screening humans to determine those having somatic mutations in the NF1 gene in tumors. Finally, the invention is directed to a method of treating a human having a tumor with somatic mutation in the NF1 gene by restoring natural regulation of ras proteins.

The NF1 gene cDNA comprises 10.7 Kb (SEQ ID NO:1) which codes for the 2818 amino acid protein, neurofibromin (SEQ ID NO:2). The NF1 gene as it exists in the human genome is a megagene having a size of about 300 Kb and comprising many exons and introns spread out over the gene. Some of the introns have been found to contain open reading frames often found in the opposite orientation as the NF1 coding sequence.

Searches of protein data bases with the amino acid sequence predicted from the NF1 gene cDNA revealed striking amino acid sequence similarities to the IRA proteins of yeast (inhibitory regulators of the ras-cAMP pathway) and also to mammalian GAPs (ras p21 GTPase-activating proteins) (7). The similarities were initially identified between a 360 amino acid region of neurofibromin (bases 3809–4888 of SEQ ID NO:1) and the catalytic domains of mammalian GAPs and the esssential domain of yeast IRA proteins. The catalytic domains of mammalian GAP (20) and IRA2 protein (21) are known to be the elements essential for binding ras proteins and stimulating their intrinsic GTPase activity. The sequence similarity, therefore, suggested that NF1 peptide may stimulate the GTPase activity of ras p21, or a ras-related protein (7). Furthermore, extensive additional similarities between the NF1 protein and yeast IRA1/IRA2 proteins extended to either side of the catalytic domain, to a total of 1560 amino acids, suggesting additional functional similarity between the two proteins.

It is highly likely that these extensive similarities among the NF1, GAP and IRA products reflect an underlying functional homology and are not due to chance. Furthermore, the properties these relationships would imply are fully commensurate with the functional characteristics that might be expected of a gene involved in an inherited neoplasia syndrome.

The GAP gene has emerged as an intriguing intermediate in the cellular transduction of extracellular signals. GAP was identified in oocyte injection studies (13) and subsequently shown to interact functionally with RAS protein, stimulating the RAS GTPase activity. This is important, because it is the GTP-bound form of RAS protein that stimulates cell proliferation; stimulation of RAS GTPase activity inhibits the effector function of RAS product (13). Recent studies have also indicated the association of GAP with the platelet-derived growth factor receptor (22); other studies suggest a possible functional interaction with the epidermal growth factor receptor (23).

However, the specific role of GAP in the signal transduction pathway remains unclear; two competing models, one with GAP upstream of RAS proteins in the pathway and one with GAP downstream, coexist (15). The discovery that only the effector domain of RAS protein interacts with GAP suggested that GAP could be the target of RAS activity (24,25). Interestingly, a recent discovery indicates that the product of the Krev-1 gene, 53% identical to RAS with highly conserved effector domains, competes for GAP with RAS product (26), Krev-1 suppresses the transformation of cells by KRAS (27).

The yeast IRA1 and IRA2 genes are inhibitors of yeast RAS1 and RAS2, previously identified as functional and structural analogs of the mammalian RAS genes. Furthermore, as with GAP, the IRA1 gene product stimulates the intrinsic GTPase activity of its target, the yeast RAS gene products (11). The two RAS genes play a key role in yeast regulatory pathways by regulating adenylate cyclase (Toda et al., 1985).

It has been shown that neurofibromin is a GAP for ras proteins (17). The 360 amino acid seqment (residues 1175–1534 of SEQ ID NO:2) exhibits GTPase-stimulating activity for ras proteins. This conclusion derives from the observation of complementation of yeast ira mutants and from assays of the biochemical activity of a purified fusion protein containing the NF1 catalytic domain. First, suppression of the heat shock-sensitive phenotype of ira mutants by expression of the relevant segment of NF1 suggested functional homology between the NF1 and IRA proteins; similar suppression of ira mutants with mammalian GAP had been shown previously (8,11). The suppression of ira mutants by NF1 peptide fragments containing a domain homologous to IRA and GAP reinforces the idea that this domain is responsible for the stimulation of GTPase activity. The putative catalytic domain of NF1 peptide expressed in $E.\ coli$ and the purified NF1 fusion protein have both exhibited biochemical activity capable of stimulating the intrinsic GTPase activity of ras proteins. Results using peptides spanning the catalytic domain raise the possibility that longer NF1 peptides may also exhibit GAP activity; indeed, one construct (pKP11) used in the yeast complementation experiments does contain substantial flanking sequence.

The GTPase-stimulating activity of NF1 peptide shares characteristics observed with yeast IRA2 and human GAP. First, NF1 peptide is incapable of stimulating the impaired GTPase activities of yeast RAS2$^{Val-19}$ or mammalian H-ras-$^{Val-12}$. Second, NF1 peptide does not stimulate the GTPase activity of an effector mutant of RAS2, Ala-42. Inability of mammalian GAP to stimulate GTPase activity of the effector mutants has been one of the hallmarks of GAP (Adari et al., 1988; Cales et al., 1988); thus, the action of NF1 on ras proteins meets many of the criteria for ras GAPs.

Expression of the NF1 catalytic domain, like the expression of GAP, complements IRA-deficient yeast and also inhibits the wild-type human H-ras protein expressed in yeast. Unlike GAP, expression of NF1 inhibits even the activated H-ras$^{Val-12}$ protein. Increases in H-ras GTPase-stimulating activity have been found in lysates of yeast expressing the NF1 catalytic region, although not as much as found in lysates of yeast expressing GAP. These last two observations suggest that the expressed NF1 protein fragment might bind more tightly to H-ras proteins than does GAP. Hence, this NF1 protein would display less GAP-like catalytic activity, yet would be capable of inhibiting the activated form of H-ras (8).

Two models exist for the function of neurofibromin (26). Neurofibromin (at least the GAP-related domain (GRD)), like GAP, may be an upstream regulatory protein for ras (or a ras-related protein) with its normal function being to down-regulate one or more members of the ras family involved in mitogenic signal transduction. This model received further support when it was shown that the proposed GAP-related domain of NF1 (NF1-GRD) could complement loss of IRA function in yeast, and that it could stimulate ras-GTPase activity in vivo and in vitro (8,16,17).

An alternate model of ras-neurofibromin interaction postulates that neurofibromin may instead (or in addition) be a downstream effector for ras. A downstream model has also been proposed for the related GAP. Mutations in the putative ras effector domain inactivate the transforming ability of ras and block GTPase activation by GAP, yet retain guanine nucleotide binding capacity (24,25). NF1-GRD interactions with effector and oncogenic mutants of ras have shown similar results, suggesting that neurofibromin may also interact with $p21^{ras}$ through its effector domain and be a target of activated ras (16–18). Either of these two models, with neurofibromin as the upstream negative regulator or downstream effector, are consistent with NF1 being a tumor suppressor gene, where the phenotype results from the loss of both alleles of the gene (30).

Recently, it has been demonstrated that neurofibromin is a negative regulator of $p21^{ras}$ (31,32). The loss of neurofibromin causes a constitutive activation of $p21^{ras}$, even in the presence of normal levels of fully functional $p120^{GAP}$. This suggests that neurofibromin is the primary negative regulator of $p21^{ras}$, at least in neural crest-derived cells, possibly owing to the higher affinity of $p21^{ras}$ for neurofibromin than for $p120^{GAP}$ (16). This finding was the first indication that neurofibromin is involved in the negative control of ras proteins in whole cells, and hence in the inhibition of cell proliferation.

Since $p21^{ras}$ does not appear to be mutationally activated in the NF1 lines (31), the increased levels of GTP-bound Ras are a consequence of diminished negative regulation by NF1. The level of GTP-bound Ras correlated inversely with the amount of NF1 protein in the four schwannoma lines (the three NF1 lines plus the rat schwannoma line). The ST88-14 line had barely detectable amounts of NF1 and significantly higher levels of GTP-bound Ras than the two NF1 lines with more modest reductions in neurofibromin. It is therefore most likely that the reduced levels of neurofibromin in the NF1 tumor lines underlie the activation of $p21^{ras}$, analogous to the effects in *S. cerevisiae* of IRA disruptions on RAS (Tanaka et al., 1990).

In accordance with the present invention, somatic mutations in the NF1 gene have been identified in human tumors other than those associated with neurofibromatosis. These tumors include colon adenocarcinomas, myelodysplastic syndrome, anaplastic astrocytoma and breast carcinoma. Each of these mutations has been found in the GAP-related domain (GRD) of neurofibromin. The mutation found in the first three of these tumors is the alteration of Lys-1423, resulting in a reduction in the GAP activity of neurofibromin of about 200–400 fold over that of the native protein. Although GAP activity is lowered, the binding affinity is unaffected. The mutations found in breast carcinoma are Phe-1477 and Pro-1466.

Although these mutations were found in the GRD of neurofibromin, tumors having reduced amounts of neurofibromin, such as would occur for missense or null mutations, also show reduced negative regulation of $p21^{ras}$. Examples of such mutations have been found in neurofibrosarcomas and malignant schwannomas of NF1 patients.

The finding that somatic mutations in the NF1 gene are found in human tumors has wide implications for the diagnosis and treatment of such tumors. Somatic mutations in the NF1 gene can be used for determining a prognosis of an individual tumor, which in turn is used to develop a course of treatment for the specific tumor. If any given tumor is analyzed and found to contain a somatic mutation in the NF1 gene, the prognosis is that the ras activity can be the focus of treatment. If the tumor does not contain a somatic mutation in the NF1 gene, then other courses of treatment will be necessary. Therapeutic treatment of any specific tumor is performed by conventional techniques once prognosis is determined.

If a tumor is found to have a somatic mutation in the NF1 gene, the tumor can be treated by the inactivation of $p21^{ras}$, which is already a target for cancer therapeutics. Furthermore, because $p120^{GAP}$ is present but apparently latent, activation of $p120^{GAP}$ would be beneficial. Finally, inhibition of GDP/GTP exchange would also counteract the loss of neurofibromin or neurofibromin GRD activity in these tumors. For example, tumor treatment can be performed using strategies based on catalytic or non-catalytic antagonism of ras function. In addition, catalytic or non-catalytic antagonism of ras function will have therapeutic potential in these tumors (60).

Tumors are screened for somatic mutations in the NF1 gene using conventional techniques including the detection of large deletions, detection of small deletions or detection of point mutations in the NF1 gene. Suitable techniques include those described in U.S. Ser. No. 07/551,531, filed Jul. 12, 1990, now U.S. Pat. No. 5,227,292 incorporated herein by reference. Useful diagnostic techniques include, but are not limited to, fluorescent in situ hybridization (FISH), direct DNA sequencing, PFGE analysis, Southern blot analysis, SSCP analysis, RNase protection assay and allele-specific oligonucleotide (ASO) dot blot analysis. An especially useful method for detecting point mutations is the PCR-SSCP method (33), as described in further detail below in the Examples. Thus, any method capable of identifying mutations in the NF1 gene can be used to screen tumors for the presence or absence of somatic mutations in the NF1 gene, providing a prognosis of the tumor for treatment modalities as described above.

The techniques described in said Ser. No. 07/551,351 (now U.S. Pat. No. 5,227,292) are as follows.

1. Detection of Large Deletions in the NF1 Gene

The availability of DNA probes from the NF1 gene provides a means of directly detecting genetic lesions that create neurofibromatosis type 1 alleles. Suitable probes include the entire normal (native) NF1 gene sequence, or fragments thereof consisting of 15 or more bases encoding a specific portion of the NF1 gene. The probes may be based on the NF1 coding sequence or on the genomic sequence, i.e., the sequence containing coding and non-coding sequence. When performed by Southern blot and dot blot procedures, this analysis is generally limited to the study of those lesions that create gross structural changes in the NF1 gene, such as deletion of many hundreds of base pairs.

The DNA for a Southern blot or dot blot analysis is isolated from a tumor sample, and the genomic DNA is isolated from the tumor in the sample, according to standard techniques. This DNA is digested with a restriction endonuclease, and the resulting fragments are separated on an agarose electrophoresis gel according to a physical property such as molecular shape or molecular weight. For the purposes of this invention, molecular shape is defined as structural configuration of the molecule (e.g., linear, circular, double-stranded or single-stranded). The DNA in the gel is transferred to a nitrocellulose filter by blotting. The filter is then probed with the appropriate cDNA or genomic sequences, such as those described herein. In order to more precisely define the location of any abnormalities detected, two or more subfragment probes can be used separately. The autoradiograms of the probed filter generate the data necessary to construct a restriction map of the NF1 locus in the somatic DNA of the tested individual.

This restriction map is compared with a control restriction map, determined by using the same restriction enzymes for digestion and the same probe. A suitable control is DNA obtained from a leucocyte DNA from a set of normal individuals. If the tested individual has an NF1 allele containing a significantly large deletion, a restriction map of his DNA, compared with the control, will contain an additional band or bands, and/or a band or bands that have lost 50% of their intensity, caused by a change in the size, or total elimination, of one or more restriction fragments by the deletion in one allele at the NF1 locus.

This screening procedure by Southern analysis will detect the existence of NF1 alleles which have large deletions. If this analysis indicates that the tested DNA from an individual has a restriction map which is different from the control map, there is a high probability that the individual contains a mutant NF1 allele.

If the test restriction map appears identical to the control, a different screening procedure can be performed to determine if the individual possesses an NF1 allele having a small deletion or point mutation. Small deletions and point mutations may be sufficient to render the allele defective, but not prevent hybridization with a probe. An example of this screening procedure is outlined below.

2. Detection of Other Mutations in the NF1 Gene

To examine a DNA sample of an individual for small deletions or point mutations in the NF1 locus, both homologs of the NF1 gene from a tumor of said individual are cloned. The cloned alleles then can be tested for the presence of nucleic acid sequence differences from the normal allele by one of the following two methods: (1) the nucleotide sequence of both the cloned alleles and normal NF1 gene or appropriate fragment (coding sequence or genomic sequence) are determined and then compared, or (2) the RNA transcriptions of the NF1 gene or gene fragment are hybridized to single stranded whole genomic DNA from an individual to be tested, and the resulting heteroduplex is treated with Ribonuclease A (RNase A) and run on a denaturing gel to detect the location of any mismatches. In more detail, these methods can be carried out according to the following procedure.

The alleles of the NF1 gene in a tumor of an individual to be tested are cloned using conventional techniques. (12–14)

For example, a tumor sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal NF1 gene. Alternatively, PCRs are performed (34,35) with primer pairs that flank the NF1 Exons. Examples of such primer pairs are set forth in Table 1.

TABLE 1

Sequences of Primers Used for PCR-SSCP Analyses

| SEQ ID NO: | Exon(s) Flanked | Sequence |
| --- | --- | --- |
| 3 | 4 | 5'-ATAATTGTTGATGTGATTTTCATTG-3' |
| 4 |   | 5'-AATTTTGAACCAGATGAAGAG-3' |
| 5 | 5 | 5'-ATCTAGTATTTTTGAGGCCTCAG-3' |
| 6 |   | 5'-CAGATATGCTATAGTACAGAAGG-3' |
| 7 | 6 | 5'-CATATCTGTTTTATCATCAGGAGG-3' |
| 8 |   | 5'-AAGTAAAATGGAGAAAGGAACTGG-3' |
| 9 | 7 | 5'-CAAAATGAAACATGGAACTTTAGA-3' |
| 10 |   | 5'-TAAGCATTAAGTACAAATAGCACA-3' |
| 11 | 7, 8, 9 | 5'-TTTATGTTTGTGCTCTAACACCAAGT-3' |
| 12 |   | 5'-ATAAATGCTAGAATGATTTCTCATGCT-3' |

The first primer in each pair lies 5' of the exon or set of exons that it amplifies.

PCRs can also be performed with primer pairs based on any sequence of the normal NF1 gene. For example, primer pairs for the large intron can be prepared and utilized. Finally, PCR can also be performed on the mRNA. The amplified products are then analyzed by single stranded conformation polymorphisms (SSCP) (35,36) to identify any differences and these are then sequenced and compared to the normal NF1 gene sequence.

The second method employs RNase A to assist in the detection of differences between the normal NF1 gene and defective genes. This comparison is performed in steps using small (~500 bp) restriction fragments of the NF1 gene as the probe. First, the NF1 gene is digested with a restriction enzyme(s) that cuts the NF1 gene sequence into fragments of approximately 500 bp. These fragments are separated on an electrophoresis gel, purified from the gel and cloned individually, in both orientations, into an SP6 vector (e.g., pSP64 or pSP65; 57). SP6-based plasmids containing inserts of NF1 gene fragments are transcribed in vitro using the SP6 transcription system well known in the art, in the presence of [$\alpha$-$^{32}$P]GTP, generating radiolabelled RNA transcripts of both strands of the NF1 gene.

Individually, these RNA transcripts are used to form heteroduplexes with the allelic DNA, as described by Myers et al. (37). Mismatches that occur in the RNA:DNA heteroduplex, owing to sequence differences between the NF1 fragment and the NF1 allele subclone from the individual, result in cleavage in the RNA strand when treated with RNase A. Such mismatches can be the result of point mutations or small deletions in the individual's NF1 allele. Cleavage of the RNA strand yields two or more small RNA fragments, which run faster on the denaturing gel than the RNA probe itself.

Any somatic mutations in the NF1 gene which are found in a specific tumor from a patient, will identify a patient who can be treated by methods which will restore normal ras function to tumors in which the ras function has been altered as a direct result of the somatic mutation in the NF1 gene.

The present invention is further detailed in the following examples, which are offered by way of illustration and are

EXAMPLE 1

General Materials and Methods

A. Patient Tissues

DNA was extracted from normal and tumor tissues of colon cancer patients, starting from either frozen (38) or paraffin-embedded specimens (39). DNA samples from normal and tumor tissues of anaplastic astrocytoma patients were kindly provided by Dr. Dan Fults. DNA samples from the peripheral blood of myelodysplastic syndrome patients were donated by Dr. Eitan Friedman. NF1 patients participating in this study are those described earlier (4). The protocols for obtaining human tissue samples used in this project have been approved by the Institutional Review Board at the University of Utah Health Sciences Center.

The colon cancer DNA sample with the Lys-to-Glu mutation was from a moderately differentiated colon adenocarcinoma from an 83-year-old female.

The myelodysplasia DNA sample with the Lys-to-Glu mutation was from a peripheral blood specimen diagnosed as refractory anemia with excess of blasts. This DNA was screened for N-ras and K-ras mutations at codons 12, 13, and 61 by an allele-specific oligonucleotide hybridization assay, and no mutations were detected. The patient was a 56-year-old woman who subsequently developed acute myelogenous leukemia.

The anaplastic astrocytoma DNA sample with the Lys-to-Gln mutation was from tumor tissue removed from the right temporal lobe of a 61-year-old male.

B. PCR Amplification

DNA samples were generated for SSCP analysis using the polymerase chain reaction (PCR) (7 min at 95° C. once; followed by 1 min at 95° C., 1 min at 58° C., 1 min at 72° C., for 35 cycles; then 10 min at 72° C.) with the primer pair FLRIN: 5'-CAAACCTTATACTCAATTCTCAACTC-3 ' (SEQ ID NO:13) , rFLRIN: 5'-AAGGGGAATTTAAGAT-AGCTAGATTATC-3 ' (SEQ ID NO:14). The reaction mixture was made up of the following: 30–70 ng of genomic DNA, a 70 μM concentration of each deoxynucleoside triphosphate, a 0.5 μM concentration of each primer, 10 mM Tris (pH 8.3), 50 mM KCl, 1.5 mM MgCl$_2$, 0.25 U of Taq polymerase, 0.25 mM spermidine, and 0.1 μl of [alpha$^{-32}$P] dCTP (3000 Ci/ml) in a volume of 10 μl.

C. SSCP Gel Analysis

PCR products were diluted 30-fold in 0.1% SDS, 10 mM EDTA, then 1:1 in 95% formamide, 20 mM EDTA, 0.05% bromphenol blue, 0.05% xylene cyanol. Products were heated at 90° C. for 3 min to denature the DNA, cooled on ice or at room temperature, and then loaded onto 4.5% nondenaturing polyacrylamide gels (49:1 polyacrylamide:methylene-bis-acrylamide (MBA)) containing 1 x or 0.5 x TBE (1 x TBE=90 mM Tris-borate [pH 7.8], 2 mM EDTA). Two conditions were routinely run for each set of samples: a gel at 4° C. and a 5% glycerol gel at room temperature. Electrophoresis was carried out for both conditions at 40 W, constant power, in the same TBE buffer as that used in the gel. After electrophoresis, the gel was transferred to Whatman 3MM paper and dried on a vacuum slab gel dryer. Autoradiography with Kodak X-Omat AR film at −70° C. with an intensifying screen overnight was usually sufficient to detect bands on film.

D. Sequencing of SSCP Conformers

Individual SSCP bands were cut directly from the dried gel, placed in 100 μl of distilled water, incubated at 37° C. with shaking for 1 hr, and centrifuged briefly to pellet debris. A 10 μl aliquot of the supernatant was used directly in a 100 μl PCR reaction. The primers used in the original amplification were used in this amplification as well, except that the 5' end of one primer contained an additional sequence consisting of the universal sequencing primer from M13, and the 5' end of the other primer included the sequence of the reverse sequencing primer. The double-stranded PCR product resulting from this amplification was purified by two centrifugation washes with a Centricon 100 column (Amicon), then sequenced following a test-site protocol suggested by Applied Biosystems, Inc. (Foster City, Calif.). This protocol involved performing the dideoxy sequencing reactions with Taq polymerase in a thermal cycler, using fluorescently tagged M13 universal or reverse sequencing primers, followed by gel electrophoresis and data collection and analysis on an Applied Biosystems model 373A automated sequencer.

E. TaqI Restriction Endonuclease Screening of the First Nucleotide in the Lys-1423 Codon In this assay, when genomic DNA is used as the template for PCR with the FLRTAQ and rFLRIN primers, amplification occurs from both the NF1 locus on chromosome 17 and the NF1 pseudogene locus on chromosome 15; this happens because the nucleotide sequence identity in these two homologous segments is greater than 90%, and neither of the primers used for PCR in this amplification is locus-specific. To make the assay specific to the NF1 locus on chromosome 17, the entire FLR exon with the intron-based primers FLRIN and rFLRIN is first amplified (as above, but without the radioactive nucleotide). This PCR amplifies only from the NF1 locus on chromosome 17, because FLRIN cannot prime in the pseudogene. This NF1 locus-specific PCR product is then diluted 1000-fold and a second PCR is performed using the FLRTAQ and rFLRIN primers to obtain the final product that is tested in the TaqI restriction endonuclease digestion assay. FLRTAQ: 5'-GAAAGGGGCT-TGAAGTTAATGTCG-3' (SEQ ID NO:15). rFLRIN: see above. PCR was performed in a 20 μl volume in a Techne MW-2 thermal cycler as follows: 5 min at 95° C., once; followed by 1 min at 95° C., 1 min at 56° C. 1 min at 72° C., 35 times; then 5 min at 72° C. Half the PCR volume was transferred to a second microtiter plate, under a drop of mineral oil. Eight units of TaqI restriction endonuclease in a 4 μl volume was then added to each sample, and the plate was incubated at 65° C. for 2 hours. Samples were then subjected to electrophoresis through a 6% agarose gel (3:1, Nusieve:SeaPlaque agarose), stained with ethidium bromide and photographed over an ultraviolet light.

F. Cloning and Manual Sequencing of the PCR Product from the FLR Exon

PCR product was generated as above, except that a BamHI site was added to the 5' end of the primer FLRIN and an EcoRI site was added to the 5' end of the primer rFLRIN. The PCR product was phenol/chloroform extracted, ethanol precipitated, and digested with BamHI and EcoRI. The digested fragment was ligated with pBluescript II phagemid vector also cut with BamHI and EcoRI. The ligation mixture was transformed into XL1-Blue supercompetent cells (Stratagene). Double-stranded sequencing of 10 independent plasmid clones was performed using Sequenase Version 2.0 (U.S. Biochemicals) according to the manufacturer's instructions.

G. PCR Subcloning of wild-type and mutant NF1 GRD

Subcloning of the wild type NF1 GRD was described by Martin et al. (16). Two-step PCR was used to generate the mutant NF1 GRD subclones. The first step included two PCR reactions with the primer pair GM444: 5'-GGAGATG-GTGTGTCGACCATGGAAGCCAAATCACAG-3' (SEQ ID NO:16); and rGRDMU 5'-ACTCTGAAGTATCT GTGACATTAACTTCAA-3' (SEQ ID NO:17), an internal antisense primer containing the mutated base as underlined—here, T to G to generate the A-to-C mutant); and the primer pair GRDMU: 5'-TTGAAGTTAATGTCA CAGATACTTCAGAGT-3' (SEQ ID NO:1B), an internal sense primer containing the mutated base as underlined); and GM446: 5'-TAGGATTCTCTAGAGCTCA TGTTTCTGGTTCTGGTGGTGGTGTTAACGTTTTCAA AGCCTTG-3' (SEQ ID NO:19) (nucleotides encoding the KT3 epitope are underlined). One µg of cDNA clone FB15 (7) was the template for each PCR reaction in a volume of 100 µM. PCR was performed with a 0.8 µM concentration of each primer, a 0.2 mM concentration of each deoxynucleoside triphosphate, 10 mM Tris (pH 8.3), 50 mM KCl, 1.5 mM $MgCl_2$, 0.01% gelatin and 2.5 U of Taq polymerase. Reactions underwent 7 min at 95° C., once, followed by 1 min at 95° C., 2 min at 55° C., 1 min at 72° C., 25 times; 10 min at 72° C. The second step involved only one PCR reaction with primer pair GM444 and GM446. In the PCR reaction, 30 µl of each PCR product from the first step was used as template. The final products obtained after 25 cycles of amplification (7 min at 95° C., once; 1 min at 95° C. 2 min at 55° C., 2 min at 72° C., 25 times; 10 min at 72° C.) were subcloned between the NcoI and XbaI sites of the baculovirus transfer vector pAcC4 (40).

H. Expression, Purification and Activity Assays of Wild Type and Mutant NF1-GRD

The methods used for biochemical analysis have been previously described (16).

EXAMPLE 2

Detection of Mutations in the NF1-GRD in Tumors

The Polymerase Chain Reaction (PCR) Single Stranded Conformation Polymorphism (SSCP) method (34) was used to screen rapidly for mutations in the GRD of the NF1 gene (NF1 GRD) in samples of DNA extracted from tumors. The first exon screened is 159 bp in length and corresponds to codons 1371–1423 of the open reading frame of the full-length NF1 cDNA (29). Located in the middle of the NF1 GRD, the protein segment encoded by this exon shows approximately 30% homology to the corresponding segments of the human GAP and yeast IRA1 and IRA2 proteins (7). A stretch of three consecutive amino acids, FLR (SEQ ID NO:20), near the middle of the exon, is completely conserved across all four proteins; FLR occurs only once in the entire 2818 aa (amino acid) sequence of the predicted NF1 protein. For convenience, this exon is referred to as the "FLR exon."

This exon received high priority in the screening strategy, because the relatively high degree of conservation of amino acid sequence across these different proteins and between species suggested that somatic mutations in this region of the gene would be likely to alter amino acid residues crucial to the function of the protein, and so result in clinical pathology.

A pair of intron-based primers (see Example 1) was used to generate a 236-bp PCR product containing the FLR exon. In most cases, paired samples of tumor DNA and accompanying constitutional DNA from the same individuals were analyzed. The DNA samples were from 22 colon adenocarcinomas paired with either peripheral blood lymphocytes or with normal colon tissue; 28 peripheral blood samples from patients with myelodysplastic syndrome (a preleukemia condition) for which no constitutional DNA was available; and 10 anaplastic astrocytoma/peripheral blood lymphocyte pairs. (Astrocytoma is one of the most common malignant brain tumors.) No tumor samples were from NF1 patients.

One tumor of each type showed a variant band on SSCP gels. FIG. 1 shows the SSCP patterns for the tumor and constitutional DNA from the one remarkable colon cancer sample and the one remarkable anaplastic astrocytoma sample. DNA sequencing (FIG. 1) showed that both variant bands were due to a single base change affecting the first nucleotide position of the Lys codon (AAG) at position 1423 in the amino acid sequence. This Lys is one of 14 aa residues in the catalytic domain that are absolutely conserved across all members of the GAP family of proteins (proteins encoded by yeast in the IRA 1, IRA 2 and SAR 1 genes and in mammals by the GAP and NF1 genes) (Xu et al., 1990a; Wang et al., 1991) suggesting that it has a crucial function in NF1 GRD activity. An A-to-G transition in colon cancer causes a Lys-to-Glu amino acid substitution. However, an A-to-C transversion in the anaplastic astrocytoma results in a Lys-to-Gln amino acid substitution. All SSCP bands derived from the constitutional DNA samples accompanying these two tumors were also sequenced, revealing only the normal AAG codon. The sequences of the tumor variant bands and the constitutional DNA bands were otherwise identical. Normal tissue DNA to accompany the one myelodysplastic syndrome sample that showed a variant SSCP pattern was not available; therefore, it was not possible to show that the variant seen reflects a somatic mutation arising in the tumor tissue. However, sequencing of the variant band from this myelodysplastic syndrome sample revealed the same GAG variant codon shown to have occurred as a somatic mutation in the colon cancer sample.

EXAMPLE 3

Detection of the Lys-to-Glu Mutation in a Patient with Neurofibromatosis 1

To detect sensitively and rapidly any change in the first nucleotide of the Lys-1423 codon in the constitutional DNA of NF1 patients, a restriction enzyme digestion-based assay was designed that uses PCR to introduce the recognition sequence of the enzyme in an allele-specific manner (Petty et al., 1991). In this assay, the presence of the normal adenine nucleotide at the first base of the codon allows cutting, but the appearance of any other nucleotide destroys the recognition site of the restriction enzyme. A PCR primer based on the sequence immediately preceding the AAG lysine codon was Used in combination with a downstream intron-based primer to amplify a short DNA segment containing the AAG lysine codon (see Example 1). By designing the upstream primer to have a non-template "G" nucleotide at its 3' terminus, the PCR product derived from normal NF1 sequence was caused to contain the sequence TCGA, in which the "G" comes from the last base in the upstream primer and the "A" comes from the first nucleotide position of the AAG lysine codon. Since TCGA is the recognition site for TaqI restriction endonuclease, PCR product from the normal NF1 sequence will be cut by TaqI. Any mutation altering the first "A" in the AAG, Lys-1423 codon prevents cutting by TaqI.

Figure 2:
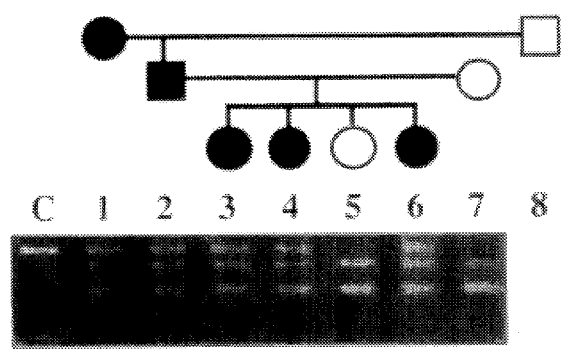
FIG. 2 shows coinheritance of the Glu-1423 mutation and neurofibromatosis 1 in the family of patient 11404. Patient 11404 (numbered "1" in the Figure) and family members are shown in the pedigree. DNA from the spouse of patient 11404 (individual 8) was not available for analysis. Persons affected by neurofibromatosis 1 are indicated by closed symbols; unaffected persons are indicated by open symbols. The TaqI restriction patterns of the PCR products from DNAs of the family members are shown at the bottom. The control lane (C) shows undigested PCR product. The homozygotes for the TaqI-cleavable allele, individuals 5 and 7, do not have neurofibromatosis 1; the heterozygotes, all other family members, carry the disease.

Lymphoblast DNA samples from 80 NF1 patients were screened by this assay, along with the mutant anaplastic astrocytoma sample and its accompanying normal lymphocyte DNA. The PCR products from 79 of the 80 NF1 patients and from the lymphocyte DNA of the anaplastic astrocytoma patient cut completely with TaqI, whereas approximately one-half of the PCR product from the anaplastic astrocytoma DNA sample did not cut with the restriction enzyme, as expected from the sequencing data for this tumor DNA sample. However, NF1 patient 11404 appeared to be heterozygous at the first nucleotide position of the AAG codon, since only half of the PCR product showed cutting with TaqI (FIG. 2, sample 1).

To determine what sequence change was responsible for this result, the entire FLR exon was PCR-amplified from the genomic DNA of patient 11404, cloned into the pBluescript II phagemid vector, and sequenced manually. Sequencing of ten independent clones revealed that five contained the normal Lys-1423 codon, AAG; however, the remaining five clones contained the unusual codon Glu1423, GAG that had been found in the colon cancer DNA sample.

EXAMPLE 4

Co-inheritance of the Glu-1423 Mutation and Neurofibromatosis 1 in the Family of Patient 11404

To further investigate the possibility that the A-to-G mutation at codon 1423 is the cause of neurofibromatosis 1 in patient 11404, DNA samples from several NF1-affected and unaffected family members of this patient were tested, using the TaqI-restriction digestion-based assay (FIG. 2). All NF1-affected descendants of patient 11404, like patient 11404 herself, were heterozygous by this assay. The one unaffected granddaughter was homozygous for the normal "A" nucleotide. The three NF1-affected granddaughters had to inherit the TaqI-resistant allele from their NF1-affected father, because their unaffected mother is homozygous for the TaqI-sensitive allele. This study shows that the Glu-1423 mutation perfectly co-inherits with neurofibromatosis 1 in this family and therefore must lie in the same copy of the NF1 gene that bears the neurofibromatosis-causing mutation. This is the expected result if the Glu-1423 mutation itself is the cause of neurofibromatosis 1 in this family.

EXAMPLE 5

Construction, Expression and Biochemical Analysis of NF1-GRD Mutant Proteins To examine the functional consequences of these mutations, site-directed mutagenesis by polymerase chain reaction (PCR) was performed to generate the A-to-C and A-to-G mutant fragments of NF1 cDNA encoding the GAP-related domain (NF1 GRD). DNA sequencing confirmed that only the desired bases were mutated. Mutant NF1 fragments with an appended sequence encoding the KT3 epitope (TPPPEPET) (SEQ ID NO:21) were cloned into the baculovirus transfer vector pAcC4, and the two mutant NF1 GRD proteins were expressed in Sf9 insect cells and purified using KT3 beads, as previously described (16).

Figure 3:
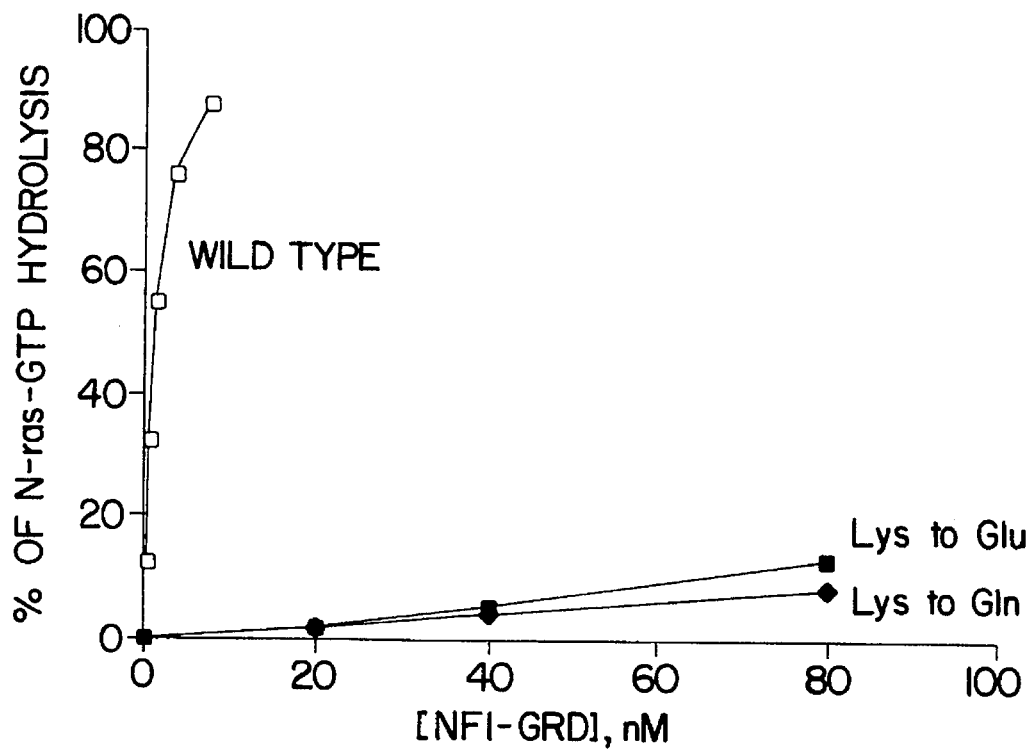
FIG. 3 shows stimulation of $p21^{N-ras}$ GTPase by wild-type and mutant NF1 GRD proteins. GTPase activities at the indicated concentrations of wild-type or mutant NF1 GRD (Lys-to-Glu and Lys-to-Gln) were measured in 20 mM HEPES (pH 7.5), 2mM $MgCl_2$, 2mM dithiothreitol (DTT), and 500 µg/ml bovine serum albumin for 10 min at 25° C. Prebinding of $p21^{ras}$ to [alpha$^{-32}$P]GTP (5000 cpm/fmol) was performed as described by Halenbeck et al. (19). Final concentration of $p21^{ras}$[alpha$^{-32}$P]GTP is 2 nM.

The ras GTPase-stimulating activities of the mutant and wild-type NF1 GRDs were determined by measuring phosphate release (16). FIG. 3 shows that the activities of both mutant proteins are greatly reduced compared with that of wild-type NF1 GRD. The activities of the Lys-to-Gln and Lys-to-Glu mutants were reduced by approximately 400- and 200-fold, respectively. $p21^{N\text{-}ras}$ was used in this assay, and the titration was performed at a low concentration of $p21^{ras}$.GTP (2 nM). Similar results were obtained using $p21^{H\text{-}ras}$.GTP.

Figure 4:
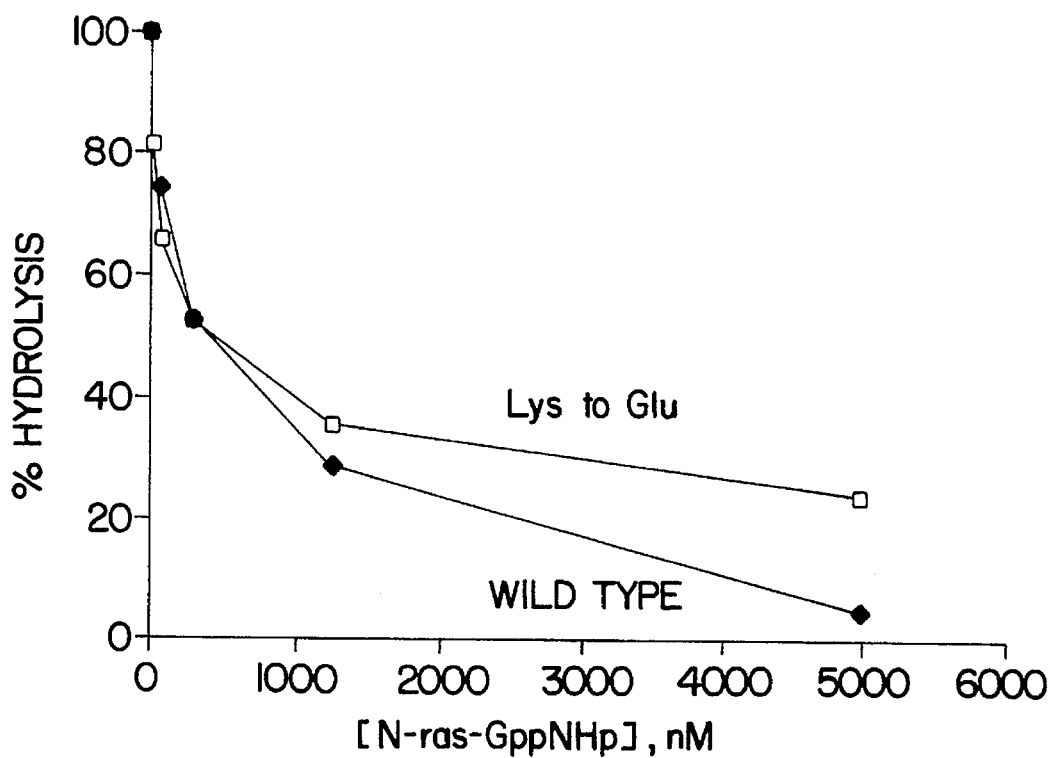
FIG. 4 shows the competitive inhibition by $p21^{ras}$.GPPNHp of $p21^{ras}$ [alpha$^{-32}$P]GTP hydrolysis by wild-type and mutant NF1-GRD proteins. The concentration of $p21^{ras}$ [alpha$^{-32}$P]GTP was approximately 1 nM. Different concentrations of the Lys-to-Glu mutant protein and the wild-type NF1 GRD were started with, to achieve a similar GAP activity; therefore, the mutant protein was approximately 500-fold more concentrated than the wild-type peptide.

The affinities of ras.GTP for the mutant and wild-type NF1 GRD proteins were estimated by measuring the ability of ras.GppNHp (guanylylimidodiphosphate, a nonhydrolyzable GTP analog) to inhibit competitively NF1 GRD-stimulated hydrolysis of $^{32}$P-labelled ras.GTP (FIG. 4). The concentration of inhibitor at which GTP hydrolysis is inhibited by 50% is approximately equal for the mutant and the wild-type NF1 GRD proteins, indicating that all bind with about the same affinity. The affinity of ras.GDP for both mutant and wild-type NF1 GRD was approximately 100-fold lower than the affinity for ras.GTP.

EXAMPLE 6

Somatic Mutation in the NF1 GRD in Breast Cancers

The polymerase chain reaction (PCR) single-stranded conformation polymorphism (SSCP) method (33) was used to screen rapidly for mutations in the GRD of the NF1 gene (NF1 GRD) in samples of DNA extracted from breast tumors from 15 patients, as described above. Two of the 15 tumors revealed an aberrant band not seen in the accompanying constitutional DNA from the same individual. The variant bands of these two tumors had identical mobilites on the gel, and PCR a second time from the original DNA stocks, followed by SSCP reproduced these results. For both tumors, the shifted SSCP bands that were observed were approximately equal in intensity to the bands of normal mobility seen within the same samples, suggesting that the number of copies of mutant and normal alleles present was approximately equal. In both cases, at base pair 4715 in codon 1477 there was a somatic mutation: TTC(Phe)→CTC(Leu). In a third tumor, base pair 4683 in codon 1466 had a somatic mutation CCT(Pro)→CTC(Leu).

Somatically acquired point mutations affecting codon 1423 of the NF1 gene have been found in DNA from a colon adenocarcinoma and an anaplastic astrocytoma. One of these mutations was also detected in a myelodysplasia for which no constitutional DNA control was available. The mutations alter a Lys residue in the catalytic domain of neurofibromin that is invariant among GAP-related proteins (7,42) and is therefore likely to be crucial for normal functioning. Indeed, the mutant NF1 GRD proteins bind with normal affinity to ras.GTP but are severely impaired in stimulating the ras GTPase. Somatic mutations in tumors were not randomly distributed within the NF1 gene: within this 159 bp exon, screened in 60 tumors, mutations were detected only in codon 1423. A mutation in this same codon was also found in a family with NF1, where it coinherits with the disease. Somatically acquired point mutations affecting codon 1477 or codon 1466 of the NF1 gene have also been found in DNA from breast carcinoma. These results suggest that at least some of the mutations in the NF1 gene that occur in the germline to cause neurofibromatosis 1 can also occur in somatic cells and contribute to the development of sporadic tumors.

One might expect that any tumor type found occasionally to harbor somatic mutations in the NF1 gene would be a tumor type with an increased incidence among NF1 patients. Indeed, astrocytomas have been reported to occur at higher rates in NF1 patients (43–46). However, colon cancers and myelodysplasias do not seem to have an increased incidence among NF1 patients. Furthermore, three generations of NF1-affected individuals in the family of patient 11404 had no history of either of these tumor types, even though the Glu-1423 mutation found in the colon and myelodysplasia tumors must be present in every somatic cell of these individuals.

There is a precedent for this apparent paradox among the hereditary neoplastic syndromes. Somatic mutations in the retinoblastoma gene are found frequently in sporadic small cell lung cancers, yet this tumor type does not have an increased incidence among individuals with hereditary retinoblastoma (47,48). Thus, somatic mutations in the Rb gene in lung cells may contribute to, and may even be necessary for, the development of the tumors. However, the mutations are not rate-limiting for tumorigenesis in this cell type.

These considerations suggest that NF1 mutations might promote growth in NF1-associated tumor types by one mechanism and promote growth in other tumor types by a somewhat different mechanism. Possible roles for neurofibromin as either an upstream regulator or a downstream effector of ras-GTP have been presented (7), but these roles are not incompatible; neurofibromin may serve both functions. In cell types where ras.GTP is growth promoting, e.g., in colon cancers (49) and myelodysplasias (50–52), the diminished capacity of mutant neurofibromins to stimulate GTP hydrolysis on ras may allow enhanced ras.GTP signaling, causing growth. In cell types where ras.GTP appears to be growth inhibiting, e.g., in Schwann cells (53) and pheochromocytomas (54,55), mutant neurofibromin may disrupt a ras.GTP neurofibromin complex that is required for transduction of the growth-inhibiting signal. This would then shift the balance of growth-regulating signals toward growth. The latter mechanism may be involved in neurofibromatosis 1, since Schwann cells proliferate excessively in the development of neurofibromas (56) and pheochromocytomas have an increased incidence among NF1 patients (45,56). Furthermore, a careful screen for activating mutations in ras genes in human pheochromolocytomas revealed none (57)—the expected result if ras.GTP inhibits growth in this cell type.

According to the above scheme, the Glu-1423 NF1 mutation would be expected to disrupt both of the proposed functions of neurofibromin (ras regulator and ras effector) in order to contribute to the development of colon and myelodysplasia tumors and cause neorofibromatosis 1; i.e., the mutant neurofibromin should be functionally null. In addition to its diminished ability to stimulate the ras-GTPase, demonstrated here, it should be blocked in signal transduction. Alternatively, the levels of the mutant neurofibromin in the cell could be very low if the mutation makes the protein unstable. Many of the NF1 mutations that have already been found in NF1 patients are also expected to be nulls, because they involve translocations, medium-sized to large deletions, or stop codons occurring within protein-coding regions of the gene (4,5). The view presented here of neurofibromin as both ras regulator and ras effector would allow the protein to function somewhat differently in different tissues. Thus, overlapping but distinct classes of mutant NF1 alleles may yet prove to be involved in the development of different tumor types.

In light of the mutations reported here, a possible role for NF1 mutations should be considered in any tumor type in which activated ras genes are frequently found. Perhaps in these tumor types NF1 mutations may be the functional complement of ras mutations and will be found in those tumor samples lacking ras mutations. Since in neurofibromatosis 1 tumor incidence is elevated in at least some tissues where ras.GTP is growth-inhibiting (see above), a role for MF1 mutations must also be considered in any tumor type in which activated ras can be shown to inhibit growth (e.g., medullary thyroid carcinoma; 58,59). Perhaps in these tumor types, NF1 mutations will be found in those tumor samples composed of cells that continue to proliferate when activated ras is introduced.

While the invention has been disclosed in this patent application by reference to the details of preferred embodiments of the invention, it is to be understood that this disclosure is intended in an illustrative rather than in a limiting sense, as it is contemplated that modifications will readily occur to those skilled in the art, within the spirit of the invention and the scope of the appended claims.

LIST OF REFERENCES

1. Stumpf, D. A. et al. (1988). *Arch. Neurol.* 45: 575–578.
2. Ricardi, V. M. and Lewis, R. A. (1988). *Am. J, Hum. Genet.* 42: 284–289.
3. U.S. Ser. No. 07/551,531, filed Jul. 12, 1990.
4. Cawthon, R. M. et al. (1990). *Cell* 62:193–201.
5. Viskochil, D. et al. (1990). *Cell* 62:187–192.
6. Wallace, M. R. et al. (1990). *Science* 249:181–186.
7. Xu, G. F. et al. (1990). *Cell* 62:599–608.
8. Ballester, R. et al., (1990). *Cell* 63:851–859.
9. Tanaka, K. et al. (1989). *Mol. Cell. Biol.* 9:757–768.
10. Tanaka, K. et al. (1990). *Cell* 60:803–807.
11. Tanaka, K. et al. (1990). *Mol. Cell Biol.* 10:4303–4313.
12. Barbacid, M. (1987). *Ann. Rev. Biochem.* 56:779–827.
13. Trahey, M. and McCormick, F. (1987). *Science* 238: 542–545.
14. McCormick, F. (1989). *Cell* 56:5–8.
15. Hall, A. (1990). *Cell* 61:921–923.
16. Martin, G. A. et al. (1990). *Cell* 63:843–849.
17. Xu, G. et al. (1990). *Cell* 63:835–841.
18. Bollag, G. and McCormick, F. (1991). *Nature* 351: 576–579.
19. Halenbeck, R. et al. (1990). *J. Biol. Chem.* 265: 21922–21928.
20. Marshall, M. S. et al. (1989). *EMBO J.* 8:1105–1110.
21. Tanaka, K. et al. (1992). *Proc. Nat. Acad Sci. USA*.
22. Kaplan, D. R. et al. (1990). *Cell* 61:125–133.
23. Ellis, C. et al. (1990). *Nature* 343:377–381.
24. Adari, H. et al. (1988). *Science* 240:518–521.
25. Cales, C. et al. (1988). *Nature* 322:548–555.
26. Frech, M. et al. (1990). *Science* 249:169–171.
27. Kitayama, H. et al. (1989). *Cell* 56:77–84.
28. Toda, T. et al. (1985). *Cell* 40:27–36.
29. Marchuk, D. A. et al. (1991). *Genomics* 11:931–940.
30. Knudson, A. G. (1985). *Cancer Res.* 45:1437–1443.
31. DeClue, J. E. et al. (1992). *Cell* 69:265–273.
32. Bosu, T. N. et al. (1992). *Nature* 356:713–715.
33. Orita, M. et al. (1989). *Genomics* 5:874–879.
34. Erlich, H. A., *PCR Technology,* Stockton Press, New York (1989).
35. Innis, M. A. et al., *PCR Protocols,* Academic Press, San Diego (1980).
36. Orita, M., et al. (1989). *Proc. Natl. Acad. Sci. USA* 86: 2766–2770.
37. Myers et al. (1985). *Science* 230:1242–1246.
38. Ausubel, F. M. et al. (1991). Current Protocols in Molecular Biology, Greene Publishing Associates and Wiley-Interscience (New York).
39. Wright, D. K. and Manos, M. M. (1990). PCR Protocols, A Guide to Methods and Applications, M. A. Innis et al., eds., Academic Press, Inc. (San Diego), pp. 153–158.

40. Luckow, V. A. and Summers, M. D. (1988). *Virology* 167:56–71.
41. Petty, E. M. et al. (1991). *Nucleic Acids Res* 19:690.
42. Wang, Y. et al. (1991). *Cell Regul.* 2:453–465.
43. Blatt, J., et al. (1986). *Cancer* 57:1225–1229.
44. Sorensen, S. A. et al. (1986). *N. Engl. J. Med.* 314:1010–1015.
45. Cohen, B. H., and Rothner, A. D. (1989). *Oncology* (Williston Park) 3: 23–30.
46. Kibirige, M. S., et al. (1989). *Pediatr. Hematol. Oncol.* 6:319–329.
47. Harbour, J. W. et al. (1988). *Science* 241: 353–357.
48. Yokota, J. et al. (1988). *Oncogene* 3:471–475.
49. Bos, J. L. et al. (1987). *Nature* 327: 293–297.
50. Liu, E. et al. (1987). *Nature* 330:186–188.
51. Lyons, J. et al. (1988). *Blood* 71:1707–1712.
52. Padua, R. A. et al. (1988). *Leukemia* 2:503–510.
53. Ridley, A. J. et al. (1988). *EMBO J.* 7:1635–1645.
54. Bar-Sagi, D. et al. (1985). *Cell* 42: 841–848.
55. Noda, M. et al. (1985). *Nature* 318:73–75.
56. Riccardi, V. M. and Eichner, J. E. (1986). Neufibromatosis: Phenotype, Natural History, and Pathogenesis, Johns Hopkins University Press (Baltimore).
57. Moley, J. F. et al. (1991). *Cancer Res.* 51: 1596–1599.
58. Nakagawa, T. et al. (1987). *Proc. Nat, Acad, Sci. USA* 94:5923–5927.
59. Nelkin, B. D. et al. (1990). *Biochem. Biophys. Res. Comm.* 170:140–146.
60. Gibbs, J. B. (1991). *Cell* 65:1–4.

---

What is claimed is:

1. A method for determining defective ras regulation at the neurofibromatosis type 1 (NF1) gene in a tumor which comprises determining said defective ras regulation by comparing the DNA sequence of the NF1 gene from said tumor with the DNA sequence of the native, non-variant NF1 gene, wherein the nucleotides within positions 3809 to 4888 of SEQ ID NO:1 are compared, wherein a mutation in the region spanning said positions in the NF1 gene of the tumor is indicative of defective ras regulation at the NF1 gene.

2. The method of claim 1 wherein said comparison is carried out by sequence analysis.

3. The method of claim 1 wherein said comparison is carried out by polymerase chain reaction-single stranded conformation polymorphism analysis.

4. The method of claim 1 wherein said comparison is carried out by RNase protection assay.

5. The method of claim 1 wherein said comparison is carried out by hybridization.

6. The method of claim 5 wherein said hybridization is fluorescent in situ hybridization.

7. The method of claim 1 wherein said comparison is carried out by single-stranded conformation polymorphism.

8. A method for determining defective ras regulation at the neurofibromatosis type 1 (NF1) gene in a tumor which comprises determining said defective ras regulation by comparing the DNA sequence of the NF1 gene from said tumor with the DNA sequence of the native, non-variant NF1 gene, wherein the nucleotide at position 4553, 4683 or 4715 of SEQ ID NO:1 is compared, wherein a mutation at one of said positions in the NF1 gene of the tumor is indicative of defective ras regulation at the NF1 gene.

9. The method of claim 8 wherein said comparison is carried out by sequence analysis.

10. The method of claim 8 wherein said comparison is carried out by polymerase chain reaction-single stranded conformation polymorphism analysis.

11. The method of claim 8 wherein said comparison is carried out by RNase protection assay.

12. The method of claim 8 wherein said comparison is carried out by hybridization.

13. The method of claim 12 wherein said hybridization is fluorescent in situ hybridization.

14. The method of claim 8 wherein said comparison is carried out by single-stranded conformation polymorphism.

* * * * *